US011236126B2

(12) United States Patent
Beigie

(10) Patent No.: US 11,236,126 B2
(45) Date of Patent: Feb. 1, 2022

(54) METHODS FOR ENHANCED REMOVAL OF IMPURITIES DURING PROTEIN A CHROMATOGRAPHY

(71) Applicant: Genzyme Corporation, Cambridge, MA (US)

(72) Inventor: Carl A. Beigie, Plainville, MA (US)

(73) Assignee: GENZYME CORPORATION, Cambridge, MA (US)

( * ) Notice: Subject to any disclaimer, the term of this patent is extended or adjusted under 35 U.S.C. 154(b) by 455 days.

(21) Appl. No.: 16/228,291

(22) Filed: Dec. 20, 2018

(65) Prior Publication Data
US 2019/0233468 A1 Aug. 1, 2019

Related U.S. Application Data

(60) Provisional application No. 62/694,387, filed on Jul. 5, 2018, provisional application No. 62/609,214, filed on Dec. 21, 2017.

(51) Int. Cl.
| | | |
|---|---|---|
| C07K 1/22 | (2006.01) | |
| C07K 16/00 | (2006.01) | |
| B01D 15/38 | (2006.01) | |
| B01D 15/42 | (2006.01) | |
| C07K 1/34 | (2006.01) | |
| C07K 1/36 | (2006.01) | |

(52) U.S. Cl.
CPC ............ *C07K 1/22* (2013.01); *B01D 15/3809* (2013.01); *B01D 15/426* (2013.01); *C07K 1/34* (2013.01); *C07K 1/36* (2013.01); *C07K 16/00* (2013.01); *C07K 2317/21* (2013.01); *C07K 2317/52* (2013.01)

(58) Field of Classification Search
CPC ...... C07K 1/22; C07K 16/00; B01D 15/3809; B01D 15/426
See application file for complete search history.

(56) References Cited

U.S. PATENT DOCUMENTS 4,871,667 A * 10/1989 Imada ................. C12P 7/44
435/142
5,750,402 A * 5/1998 Guri .................... C12N 5/0025
435/431

FOREIGN PATENT DOCUMENTS

WO WO2007081906 A2 7/2007
WO WO2011073389 A1 6/2011

OTHER PUBLICATIONS

Aboulaich, N. (2014, e-pub. Jul. 26, 2014). "A Novel Approach to Monitor Clearance of Host Cell Proteins Associated with Monoclonal Antibodies", Biotechnol Prog. 30(5):1114-1124.
Chollangi, S. et al. (Nov. 2015, e-pub. Jul. 31, 2015). "Development of Robust Antibody Purification by Optimizing Protein-A Chromatography in Combination With Precipitation Methodologies", Biotechnol Bioeng. 112 (11):12292-2304.
(Continued)

*Primary Examiner* — Daniel E Kolker
*Assistant Examiner* — James L Rogers
(74) *Attorney, Agent, or Firm* — Morrison & Foerster LLP

(57) ABSTRACT

Provided herein are methods relating to the purification of a polypeptide comprising an Fc region (e.g., an antibody) via protein A chromatography; methods relating to the use of a wash solution comprising a benzoate salt and/or benzyl alcohol during protein A chromatography; and methods of adjusting a harvest using sodium benzoate prior to protein A chromatography.

20 Claims, 9 Drawing Sheets

(56) References Cited

OTHER PUBLICATIONS

International Search Report and Written Opinion dated Apr. 2, 2019, for PCT Application No. PCT/US2018/066890 filed on Dec. 20, 2018, 71 pages.
Millipore Corporation. (2006) "Increasing Purity on Prosep®—VA Affinity Chromatography Media Using An Intermediate Wash Step", Technical Brief, Bruchure LitNo TB 1026ENOO 7/06 06-270 , Printed in the U.S.A., © 2006 Millipore Corporation, Billerica, MA 01821 U.S.A., 4 pages.

\* cited by examiner

METHODS FOR ENHANCED REMOVAL OF IMPURITIES DURING PROTEIN A CHROMATOGRAPHY

CROSS-REFERENCE TO RELATED APPLICATIONS

This application claims the priority benefit of U.S. Provisional Application No. 62/609,214, filed Dec. 21, 2017, and U.S. Provisional Application No. 62/694,387, filed Jul. 5, 2018, the contents of which are incorporated herein by reference in their entirety.

FIELD OF THE INVENTION

The present disclosure relates to methods of purifying a polypeptide comprising an Fc region (e.g., an antibody) via protein A chromatography.

BACKGROUND

Antibodies, and other Fc region-containing proteins (such as immunoadhesins), have found widespread use in pharmaceutical/therapeutic applications. The use of these molecules (e.g., in human patients) necessitates careful purification away from any contaminants/impurities that may arise during protein production. Purification of therapeutic proteins is often achieved utilizing one or more chromatographic purification steps; a particularly useful type of chromatographic purification of proteins that contain an immunoglobulin Fc region (e.g., an antibody) is protein A chromatography. However, host cell proteins (HCPs) have been shown to co-elute with antibodies during conventional capture-mode protein chromatography (including protein A chromatography), which may be problematic for downstream applications of these antibodies. Typically, one or more wash steps are employed following binding of the product (e.g., a protein containing an immunoglobulin Fc region) to the chromatography resin prior to elution. Unfortunately, current wash formulations made up of salt and a buffering species may not be sufficient to break up the interaction of HCPs and other impurities with various monoclonal antibody (mAb) products. Accordingly, there is a need for improved purification methods (e.g., the implementation of new wash formulations) that reduce the concentration/numbers of impurities (e.g., HCPs) that co-purify with antibodies (e.g., during protein A affinity chromatography).

All references cited herein, including patent applications, patent publications, non-patent literature, and UniProtKB/Swiss-Prot Accession numbers are herein incorporated by reference in their entirety, as if each individual reference were specifically and individually indicated to be incorporated by reference.

BRIEF SUMMARY

To meet the above and other needs, disclosed herein are improved methods of purifying Fc region-containing polypeptides away from one or more impurities. These methods comprise contacting a Protein A chromatography matrix with a sample (e.g., a cell lysate) comprising (i) a polypeptide comprising an Fc region and (ii) one or more impurities, and washing the matrix with a wash solution having a pH of about 4.0-10.0 and comprising a benzoate salt and/or benzyl alcohol. The present disclosure is based, at least in part, on the surprising finding that use of benzoate salt (e.g., sodium benzoate) and/or benzyl alcohol in a wash solution at a pH of about 4.0-10.0 during protein A chromatography provides superior clearance of impurities (e.g., host cell impurities) over currently utilized wash formulations (See FIG. 1, Example 1). The present disclosure is also based, at least in part, on the finding that the inclusion of one or more additional components selected from benzenesulfonate (e.g., sodium benzenesulfonate), caprylic acid, hexylene glycol, and/or arginine may further improve the clearance of impurities when included in the wash solution (See FIGS. 2 and 3, Example 1).

Accordingly, in one aspect, provided herein is a method of purifying a polypeptide comprising an Fc region, the method comprising the steps of: (a) contacting a Protein A chromatography matrix with a sample comprising (i) the polypeptide comprising the Fc region and (ii) one or more impurities, under a condition that the polypeptide comprising the Fc region binds to Protein A; and (b) washing the matrix with a wash solution, wherein the wash solution comprises one or both of (i) a benzoate salt at a concentration of about 0.1 M to about 1.0 M and (ii) benzyl alcohol at a concentration of about 0.5% to about 4% volume/volume (v/v), and wherein the wash solution has a pH of about 4.0 to about 10.0. In some embodiments, the wash solution comprises: (1) benzoate salt; (2) benzyl alcohol; or (3) benzoate salt and benzyl alcohol. In some embodiments, the benzoate salt is at a concentration from about 0.1 M to about 0.5 M. In some embodiments that may be combined with any of the preceding embodiments, the benzoate salt is a benzoate alkali salt. In some embodiments that may be combined with any of the preceding embodiments, the benzoate salt is sodium benzoate. In some embodiments, the sodium benzoate is at a concentration from about 0.1 M to about 0.3 M. In some embodiments, the sodium benzoate is at a concentration of about 0.3 M. In some embodiments, the sodium benzoate is at a concentration of about 0.5 M. In some embodiments that may be combined with any of the preceding embodiments, the benzyl alcohol is at a concentration from about 1% to about 4% (v/v). In some embodiments that may be combined with any of the preceding embodiments, the benzyl alcohol is at a concentration from about 1% to about 2% (v/v). In some embodiments that may be combined with any of the preceding embodiments, the benzyl alcohol is at a concentration of about 2% (v/v). In some embodiments that may be combined with any of the preceding embodiments, the benzyl alcohol is at a concentration of about 4% (v/v).

In some embodiments that may be combined with any of the preceding embodiments, the wash solution further comprises a buffering agent. In some embodiments, the buffering agent is selected from phosphate, tris, arginine, acetate, and citrate. In some embodiments, the buffering agent is at a concentration of about 10 mM to about 50 mM or about 10 mM to about 500 mM. In some embodiments, the buffering agent is at a concentration of about 50 mM. In some embodiments, the buffering agent is at a concentration of about 500 mM. In some embodiments, the wash solution has a pH of about 5.0 to about 10.0. In some embodiments, the wash solution has a pH of about 5.0 to about 9.0. In some embodiments, the wash solution has a pH of about 5.0, about 6.0, about 7.0, about 8.0, about 9.0, or about 10.0.

In some embodiments that may be combined with any of the preceding embodiments, the wash solution further comprises sodium benzenesulfonate. In some embodiments, the sodium benzenesulfonate is at a concentration of about 0.1 M to about 0.5 M. In some embodiments that may be combined with any of the preceding embodiments, the wash solution further comprises caprylic acid. In some embodiments, the caprylic acid is at a concentration of about 10 mM to about 50 mM. In some embodiments that may be combined with any of the preceding embodiments, the wash solution further comprises hexylene glycol. In some embodiments, the hexylene glycol is at a concentration of about 1% to about 10% (v/v). In some embodiments that may be combined with any of the preceding embodiments, the wash solution further comprises creatine. In some embodiments, the creatine is at a concentration of about 10 mM to about 100 mM. In some embodiments that may be combined with any of the preceding embodiments, the wash solution further comprises arginine. In some embodiments, the arginine is at a concentration of about 0.1 M to about 1.0 M. In some embodiments, the arginine is at a concentration of about 0.5 M. In some embodiments, the arginine is arginine-HCl. In some embodiments, the wash solution comprising arginine has a pH of about 4.0 to about 6.0. In some embodiments, the wash solution comprising arginine has a pH of about 8.0 to about 10.0. In some embodiments that may be combined with any of the preceding embodiments, the wash solution further comprises one or more non-buffering salts. In some embodiments, the one or more non-buffering salts are selected from sodium chloride, sodium bromide, potassium chloride, potassium bromide, magnesium chloride, magnesium bromide, calcium chloride, calcium bromide, and any combinations thereof. In some embodiments, the one or more non-buffering salts are sodium chloride and/or potassium chloride. In some embodiments, the one or more non-buffering salts are at a concentration of about 0.1 M to about 1.0 M.

In some embodiments that may be combined with any of the preceding embodiments, the wash solution is a solution selected from: (i) a solution comprising sodium benzoate at a concentration of about 0.5 M, and sodium bicarbonate at a concentration of about 50 mM, having a pH of about 10.0; (ii) a solution comprising sodium benzoate at a concentration of about 0.5 M, benzyl alcohol at a concentration of about 2%, arginine at a concentration of about 0.5 M, and sodium phosphate at a concentration of about 50 mM, having a pH of about 9.0; (iii) a solution comprising sodium benzoate at a concentration of about 0.5 M and benzyl alcohol at a concentration of about 2% (v/v), having a pH of about 7.0; (iv) a solution comprising sodium benzoate at a concentration of about 0.5 M, benzyl alcohol at a concentration of about 2% (v/v), and sodium chloride at a concentration of about 0.5 M, having a pH of about 7.0; (v) a solution comprising hexylene glycol at a concentration of about 10% (v/v), sodium benzoate at a concentration of about 0.5 M, and benzyl alcohol at a concentration of about 2% (v/v), having a pH of about 7.0; (vi) a solution comprising benzenesulfonate at a concentration of about 0.5 M, sodium benzoate at a concentration of about 0.5 M, and benzyl alcohol at a concentration of about 2% (v/v), having a pH of about 7.0; (vii) a solution comprising caprylic acid at a concentration of about 50 mM, sodium benzoate at a concentration of about 0.5 M, arginine at a concentration of about 0.5 M, and sodium chloride at a concentration of about 0.5 M, having a pH of about 7.0; (viii) a solution comprising sodium benzoate at a concentration of about 0.5 M, benzyl alcohol at a concentration of about 2% (v/v), and arginine at a concentration of about 0.5 M, having a pH of about 6.0; (ix) a solution comprising sodium benzoate at a concentration of about 0.5 M, benzyl alcohol at a concentration of about 2% (v/v), and arginine at a concentration of about 0.5 M, having a pH of about 5.0; (x) a solution comprising benzyl alcohol at a concentration of about 4% (v/v), having a pH of about 5.0 to about 10; (xi) a solution comprising benzyl alcohol at a concentration of about 4% (v/v), having a pH of about 9.0; and (xii) a solution comprising benzyl alcohol at a concentration of about 2% (v/v) and arginine at a concentration of about 0.5 M, having a pH of about 5.0.

In some embodiments that may be combined with any of the preceding embodiments, the method further comprises a step of washing the matrix with a first solution prior to washing the matrix with the wash solution as described above. In some embodiments, the first solution comprises a buffer selected from a phosphate buffer, a tris buffer, an acetate buffer, a carbonate buffer, a citrate buffer, and any combinations thereof. In some embodiments, the first solution comprises the buffer at a concentration of about 10 mM to about 100 mM or about 10 mM to about 500 mM. In some embodiments, the first solution is a phosphate buffer.

In some embodiments that may be combined with any of the preceding embodiments, the method further comprises a step of washing the matrix with a second solution after washing the matrix with the wash solution as described above. In some embodiments, the second solution comprises a buffer selected from a phosphate buffer, a tris buffer, an acetate buffer, a carbonate buffer, a citrate buffer, and any combinations thereof. In some embodiments, the second solution comprises the buffer at a concentration of about 10 mM to about 100 mM or about 10 mM to about 500 mM. In some embodiments, the second solution has a pH of about 5.0 to about 7.0. In some embodiments, the second solution comprises substantially low salt or no salt.

In some embodiments that may be combined with any of the preceding embodiments, the method further comprises a step of contacting the Protein A chromatography matrix with an elution solution after one or more washings steps. In some embodiments, the method further comprises the step of collecting an eluate comprising the polypeptide comprising the Fc region. In some embodiments, the method further comprises a step of filtering the eluate via depth filtration. In some embodiments, the eluate comprises less than about 500 parts per million (ppm) of the one or more impurities.

In some embodiments that may be combined with any of the preceding embodiments, applying the methods described herein results in the polypeptide comprising the Fc region being purified away from the one or more impurities to a higher degree than a corresponding method lacking the step of washing the matrix with the wash solution. In some embodiments that may be combined with any of the preceding embodiments, the one or more impurities are host cell proteins (HCPs). In some embodiments, the one or more HCPs are selected from phospholipases (e.g. Putative Phospholipase B-like 2), clusterin, serine proteases, elongation factors, and any combinations thereof. In some embodiments, the host cell is a mammalian host cell. In some embodiments, the host cell is a Chinese hamster ovary (CHO) cell.

In some embodiments, the Fc region is a human Fc region. In some embodiments, the human Fc region comprises a human IgG1, IgG2, or IgG4 Fc region. In some embodiments, the Fc region is a mouse Fc region. In some embodiments, the mouse Fc region comprises a mouse IgG1, IgG2, or IgG3 Fc region. In some embodiments that may be combined with any of the preceding embodiments, the polypeptide comprising the Fc region is an antibody. In some embodiments, the antibody is a human antibody, a humanized antibody, or a chimeric antibody. In some embodiments, the antibody is a monoclonal antibody. In some embodiments, the antibody is a bispecific antibody or a trispecific antibody.

In some embodiments, any one of the methods above further comprises, before contacting the Protein A chromatography matrix with a sample comprising (i) the polypeptide comprising the Fc region and (ii) one or more impurities, adjusting a harvest comprising the polypeptide comprising the Fc region to achieve a final concentration of a benzoate salt of between about 0.1 M and about 0.5 M and a pH between about 7.0 and about 9.0, e.g., to produce the sample comprising (i) the polypeptide comprising the Fc region, and (ii) one or more impurities. In some embodiments, the benzoate salt is a benzoate alkali salt. In some embodiments, the benzoate salt is sodium benzoate. In some embodiments, the final concentration of the benzoate salt in the harvest is between about 0.4M and about 0.5M. In some embodiments, the pH of the harvest following adjustment is between about 7.0 and about 8.0. In some embodiments, the pH of the harvest following adjustment is between about 8.0 and about 9.0. In some embodiments, the harvest is generated from a culture comprising a host cell engineered to express the polypeptide. In some embodiments, the host cell is a eukaryotic host cell. In some embodiments, the eukaryotic host cell is a Chinese Hamster Ovary (CHO) cell. In some embodiments, the harvest is clarified prior to the adjusting. In some embodiments, the harvest is clarified following the adjusting.

In a related aspect, provided is a method of purifying a polypeptide comprising an Fc region, the method comprising the steps of: (A) adjusting a harvest comprising the polypeptide comprising the Fc region to achieve a final concentration of a benzoate salt of about 0.1M and about 0.5M and a pH between about 7.0 and about 9.0, e.g., to produce a sample comprising (i) the polypeptide comprising the Fc region, and (ii) one or more impurities; and (B) contacting the sample with at least one chromatography matrix. In some embodiments, the at least one chromatography matrix comprises an affinity chromatography matrix. In some embodiments, the affinity chromatography matrix is a Protein A chromatography matrix or a Protein G chromatography matrix. In some embodiments, the method further comprises a step of contacting the at least one chromatography matrix with at least one wash solution. In some embodiments, the method further comprises a step of contacting the at least one chromatography matrix with an elution solution. In some embodiments, the method further comprises the step of collecting an eluate comprising the polypeptide comprising the Fc region. In some embodiments, the method further comprises a step of filtering the eluate via depth filtration. In some embodiments, the eluate comprises less than about 500 parts per million (ppm) of the one or more impurities.

In some embodiments, the benzoate salt is a benzoate alkali salt. In some embodiments, the benzoate salt is sodium benzoate. In some embodiments, the final concentration of the benzoate salt in the harvest is between about 0.4M and about 0.5M. In some embodiments, the pH of the harvest following adjustment is between about 7.0 and about 8.0. In some embodiments, the pH of the harvest following adjustment is between about 8.0 and about 9.0. In some embodiments, the harvest is generated from a culture comprising a host cell engineered to express the polypeptide. In some embodiments, the host cell is a eukaryotic host cell. In some embodiments, the eukaryotic host cell is a Chinese Hamster Ovary (CHO) cell. In some embodiments, the harvest is clarified prior to the adjusting. In some embodiments, the harvest is clarified following the adjusting. In some embodiments, the method results in the polypeptide comprising the Fc region being purified away from the one or more impurities to a higher degree than a corresponding method lacking the step of adjusting the harvest comprising the polypeptide comprising the Fc region to produce the sample. In some embodiments, the one or more impurities are host cell proteins (HCPs). In some embodiments, the one or more HCPs are selected from the group consisting of phospholipases, clusterin, serine proteases, elongation factors, and any combinations thereof. In some embodiments, the HCP is Putative Phospholipase B-like 2 (PLBL2). In some embodiments, the Fc region is a human Fc region. In some embodiments, the human Fc region comprises a human IgG1, IgG2, or IgG4 Fc region. In some embodiments, the Fc region is a mouse Fc region. In some embodiments, the mouse Fc region comprises a mouse IgG1, IgG2, or IgG3 Fc region. In some embodiments, the polypeptide comprising the Fc region is an antibody. In some embodiments, the antibody is a human antibody, a humanized antibody, or a chimeric antibody. In some embodiments, the antibody is a monoclonal antibody. In some embodiments, the antibody is a bispecific antibody or a trispecific antibody.

It is to be understood that one, some, or all of the properties of the various embodiments described above and herein may be combined to form other embodiments of the present disclosure. These and other aspects of the present disclosure will become apparent to one of skill in the art. These and other embodiments of the present disclosure are further described by the detailed description that follows.

BRIEF DESCRIPTION OF THE DRAWINGS

FIG. 2A shows the concentration of HCP-A in antibody samples eluted from protein A columns after being washed with 2% benzyl alcohol±0.5M sodium benzoate and/or 0.5M arginine in comparison to a control wash, as assessed by ELISA.

FIG. 2B shows the concentration of HCP-A in antibody samples eluted from protein A columns after being washed with various wash solutions at pH of 9.0 or 10.0 in comparison to a control wash, as assessed by ELISA.

FIG. 4A shows the concentration of generic HCP in antibody samples eluted from protein A columns after being washed with 0.5 M Arginine, 0.5 M Sodium Benzoate, or 4% Benzyl Alcohol in comparison to a process control wash, as assessed by ELISA. FIG. 4B shows the concentration of generic PLBL2 in antibody samples eluted from protein A columns after being washed with 0.5 M Arginine, 0.5 M Sodium Benzoate, or 4% Benzyl Alcohol in comparison to a process control wash, as assessed by ELISA.

FIG. 6A shows the percentage in off-column yield decreases linearly from 93.1% to 78.1% as the loading density of protein A columns increases from 40 g/L to 60 g/L. FIG. 6B shows the level of PLBL2 washed out of the protein A column decreases from 32.1 ppm to 17 ppm as the loading density of protein A columns increases from 40 g/L to 60 g/L.

DETAILED DESCRIPTION

Figure 1:
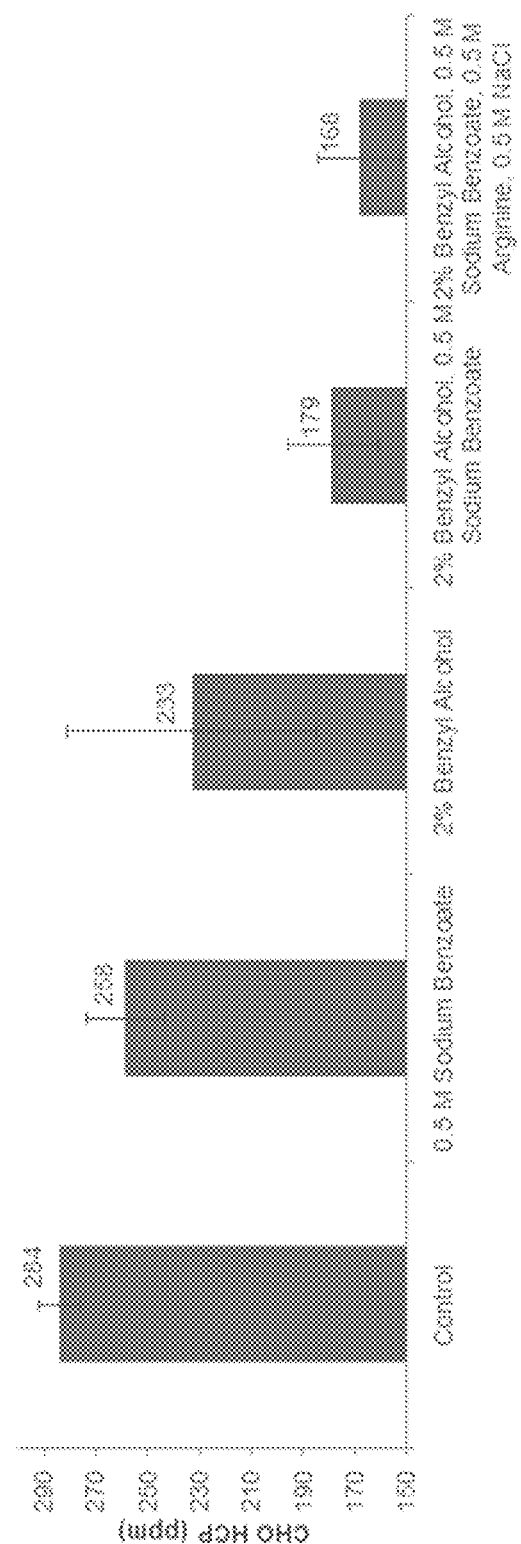
FIG. 1 shows the concentration of Chinese hamster ovary (CHO) host cell protein (HCP) impurities in antibody samples eluted from protein A columns after being washed with the indicated control or test wash solutions.

Described herein are methods of reducing the number of impurities (e.g., host cell protein impurities) co-purified during protein A-based isolation of Fc-region containing proteins. The methods of the present disclosure apply an intermediate wash step using a novel wash solution containing a benzoate salt and/or benzyl alcohol that has been shown to significantly reduce the levels of host cell protein impurities in the eluates collected during protein A affinity chromatography (See Examples 1 and 2). The inclusion of one or more additives (e.g., benzenesulfonate, caprylic acid, hexylene glycol, creatine, and/or arginine) in this novel wash solution further improves the clearance of impurities from a protein eluate containing an Fc-region containing protein after capture and elution from a protein A matrix.

I. Definitions

Before describing the present disclosure in detail, it is to be understood that this present disclosure is not limited to particular compositions or biological systems, which can, of course, vary. It is also to be understood that the terminology used herein is for the purpose of describing particular embodiments only, and is not intended to be limiting.

As used in this specification and the appended claims, the singular forms "a", "an" and "the" include plural referents unless the content clearly dictates otherwise. Thus, for example, reference to "a molecule" optionally includes a combination of two or more such molecules, and the like.

The term "about" as used herein refers to the usual error range for the respective value readily known to the skilled person in this technical field. Reference to "about" a value or parameter herein includes (and describes) embodiments that are directed to that value or parameter per se.

It is understood that aspects and embodiments of the present disclosure described herein include "comprising," "consisting," and "consisting essentially of" aspects and embodiments.

The term "and/or" as used herein a phrase such as "A and/or B" is intended to include both A and B; A or B; A (alone); and B (alone). Likewise, the term "and/or" as used herein a phrase such as "A, B, and/or C" is intended to encompass each of the following embodiments: A, B, and C; A, B, or C; A or C; A or B; B or C; A and C; A and B; B and C; A (alone); B (alone); and C (alone).

The term "polypeptide" or "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component or toxin. Also included within the definition are, for example, polypeptides containing one or more analogs of an amino acid (including, for example, unnatural amino acids, etc.), as well as other modifications known in the art.

The term "antibody" is used herein in the broadest sense, and specifically includes monoclonal antibodies (including full length monoclonal antibodies), polyclonal antibodies, multispecific antibodies (e.g., bispecific antibodies, trispecific antibodies, etc.), antibody fragments, or synthetic polypeptides carrying one or more CDR or CDR-derived sequences so long as the polypeptides exhibit the desired activity. Antibodies (Abs) and immunoglobulins (Igs) are glycoproteins having the same structural characteristics. Generally, antibodies are considered Igs with a defined or recognized specificity. Thus, while antibodies exhibit binding specificity to a specific target, immunoglobulins include both antibodies and other antibody-like molecules which lack target specificity. The antibodies of the present disclosure may be of any class (e.g., IgG, IgE, IgM, IgD, IgA, etc.), or subclass (e.g., IgG1, IgG2, IgG2a, gG3, IgG4, IgA1, IgA2, etc.). The "type" and "class" and "subtype" and "subclass" are used interchangeably herein. Native or wild-type (obtained from a non-artificially manipulated member of a population) antibodies and immunoglobulins are usually heterotetrameric glycoproteins of about 150,000 Daltons, composed of two identical light (L) chains and two identical heavy (H) chains. Each heavy chain has at one end a variable domain (VH) followed by a number of constant domains. Each light chain has a variable domain (VL) at one end, and a constant domain at the other end. Antibodies described herein may be human antibodies, humanized antibodies, non-human animal (e.g., mouse, rat, hamster, rabbit, camelid, etc.) antibodies, or chimeric antibodies.

The term "variable" in the context of a variable domain of antibodies may refer to certain portions of the pertinent molecule which differ extensively in sequence between and among antibodies, and are used in specific recognition and binding or a particular antibody for its particular target. However, the variability is not evenly distributed through the variable domains of antibodies. The variability is concentrated in three segments called complementarity determining regions (CDRs) also known as hypervariable regions, both in the light chain and heavy chain variable domains. The more highly conserved portions of variable domains are called the framework (FR) regions or sequences. The variable domains of native heavy and light chains each comprise four FR regions, largely adopting a β-sheet configuration, connected by three CDRs, which form loops connecting, and in some cases forming part of, the β-sheet structure. The CDRs in each chain are held together often in proximity by the FR regions and, with the CDR2 from the other chain, contribute to the formation of the target (epitope or determinant) binding site of antibodies (see Kabat et al. Sequences of Proteins of Immunological Interest, Nation Institute of Health, Bethesda, Md. (1987)). As used herein, numbering of immunoglobulin amino acid residues is done according to the immunoglobulin amino acid residue numbering system of Kabat et al., unless otherwise indicated. One CDR can carry the ability to bind specifically to the cognate epitope.

The term "hinge" or "hinge region" as used herein, may refer to the flexible polypeptide comprising the amino acid between the first and second constant domains of an antibody.

The term "bispecific antibodies" may refer to molecules which combine the antigen binding sites of two antibodies within a single molecule. Thus, a bispecific antibody is able to bind two different antigens simultaneously.

The term "monoclonal antibody" used herein may refer to an antibody obtained from a population of substantially homogenous antibodies, i.e., the individual antibodies comprising the population are identical except for possible naturally occurring mutations that may be present in minor amounts. Monoclonal antibodies herein specifically include "chimeric" antibodies in which a portion of the heavy and/or light chains is identical or homologous to corresponding sequences in antibodies derived from a particular species or belonging to a particular antibody class or subclass, with the remained of the chain(s) identical with or homologous to corresponding sequences in antibodies derived from another species or belonging to another antibody class or subclass, as well as fragments of such antibodies, so long as they retain the desired activity.

The term "multivalent antibody" or "polyvalent antibody" as used herein may refer to an antibody comprising two or more antigen binding sites, thus being able to bind two or more antigens, which may have the same or a different structure, simultaneously. The term "bivalent" means that the antibody comprises two antigen binding sites. The term "tetravalent" means that the antibody comprises four antigen binding sites.

The term "antigen binding site" as used herein may refer to the portion of the antibody which comprises the area which specifically binds to and is complementary to part or all of an antigen. Where an antigen is large, an antibody may only bind to a particular part of the antigen, which part is termed an epitope. An antigen binding domain may be provided by one or more antibody variable domains, and may be made of the association of an antibody light chain variable domain (VL) and an antibody heavy chain variable domain (VH).

"Humanized" forms of non-human (e.g., murine) antibodies are chimeric immunoglobulins, immunoglobulin chains, or fragments thereof which contain sequences derived from non-human immunoglobulin, as compared to a human antibody. In general, a humanized antibody will comprise substantially all of one, and typically two, variable domains, in which all or substantially all of the CDR regions correspond to those of a non-human immunoglobulin and all or substantially all of the FR regions are those of a human immunoglobulin template sequence. The humanized antibody may also comprise at least a portion of an immunoglobulin constant region, typically that of the human immunoglobulin template chosen. In general, the goal is to have an antibody molecule that is minimally immunogenic in a human. Thus, it is possible that one or more amino acids in one or more CDRs can also be changed to one that is less immunogenic to a human host, without substantially minimizing the specific binding function of the one or more CDRs to the target. Alternatively, the FR can be non-human but those amino acids most immunogenic are replaced with ones less immunogenic. Nevertheless, CDR grafting (as described above) is not the only way to obtain a humanized antibody. For example, modifying jus the CDR regions may be insufficient as it is not uncommon for framework residues to have a role in determining the three-dimensional structure of the CDR loops and the overall affinity of the antibody for its ligand. Hence, any means can be practiced so that the non-human parent antibody molecules is modified to be one that is less immunogenic to a human, and global sequence identity with a human antibody is not always a necessity.

The term "impurity" may refer to any foreign or undesirable molecule that is present in a solution (such as a sample comprising a polypeptide comprising an Fc region). An impurity may be a biological (molecule) (e.g., a macromolecule) such as DNA, RNA, or protein that is also present in a sample containing a protein of interest. Impurities may include undesirable protein variants (e.g., aggregated proteins, misfolded proteins, underdisulfide-bonded proteins, fragments, etc.), other proteins from host cells, components from cell culture medium, molecules that are part of an absorbent used for affinity chromatography (e.g., protein A), endotoxins, nucleic acids, viruses, etc.

II. Methods of Isolating and/or Purifying FC-Region Containing Polypeptides

Overview

Certain aspects of the present disclosure relate to a method of purifying a polypeptide comprising an Fc region (e.g., an antibody) via protein A chromatography. In some embodiments, the method comprises the steps of: contacting a protein A chromatography matrix or resin with a sample comprising (1) a polypeptide comprising an Fc region (e.g., an antibody) and (2) one or more impurities (e.g., host cell impurities) under a condition that the polypeptide comprising the Fc region (e.g., the antibody) binds to protein A; and washing the matrix with a wash solution comprising a benzoate salt and/or benzyl alcohol. In some embodiments, the wash solution comprises the benzoate salt at a concentration of about 0.1 M to about 1.0 M. In some embodiments, the wash solution comprises the benzyl alcohol at a concentration of about 0.5% to about 4% volume/volume (v/v). In some embodiments, the wash solution has a pH of about 4.0 to about 10.0. In some embodiments, the wash solution comprises one or more additives (e.g., one or more of benzenesulfonate, caprylic acid, hexylene glycol, a non-buffering salt (such as sodium chloride), creatine, and/or arginine). In some embodiments, the wash solution further comprises a buffering agent. In some embodiments, a harvest that comprises the polypeptide comprising an Fc region is adjusted to achieve a final concentration of a benzoate salt of between about 0.1 M and 0.5 M and a pH between about 7 and about 9 to produce the sample comprising (1) a polypeptide comprising an Fc region (e.g., an antibody) and (2) one or more impurities (e.g., host cell impurities).

Contacting a Sample with a Protein A Matrix or Resin

Certain aspects of the present disclosure relate to methods of purifying a polypeptide comprising an Fc region (e.g., an antibody) via protein A chromatography. In some embodiments, the method comprises a step of: contacting a protein A chromatography matrix or resin with a sample comprising (1) a polypeptide comprising an Fc region (e.g., an antibody) and (2) one or more impurities (e.g., host cell impurities) under a condition that the polypeptide comprising the Fc region (e.g., the antibody) binds to protein A.

In some embodiments, the present disclosure relates to methods of purifying a polypeptide comprising an Fc region (e.g., an antibody, an immunoadhesin, a fusion protein, etc.) from a sample (e.g., a cell lysate sample, a cell culture supernatant sample, etc.). In some embodiments, the sample is a cell culture supernatant (e.g., a supernatant from cells, such as CHO cells, engineered to produce and secrete the polypeptide), or is derived from a cell culture supernatant (e.g., a partially purified cell culture supernatant sample). In some embodiments, the polypeptide comprising an Fc region is a secreted polypeptide. In some embodiments, the Fc region is the C-terminal region of an immunoglobulin heavy chain, and may include native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof (the numbering of the residues in the Fc region is that of the EU index as in Kabat). The Fc region of an immunoglobulin generally comprises two constant domains, CH2 and CH3, and optionally comprises a CH4 domain. In some embodiments, the Fc region is an Fc region obtained from any suitable immunoglobulin, such as IgG1 IgG2, IgG3, or IgG4 subtypes, IgA, IgE, IgD or IgM. In some embodiments, the polypeptide comprises an Fc region having the amino acid sequence of a human Fc region, a non-human animal Fc region (e.g., a mouse, rat, rabbit, hamster, etc.), or any combinations thereof. In some embodiments, the Fc region is a mouse Fc region. In some embodiments, the mouse Fc region comprises a mouse IgG1, IgG2, or IgG3 Fc region. In some embodiments, the Fc region is a human Fc region. In some embodiments, the human Fc region comprises a human IgG1, IgG2, and/or IgG4 Fc region.

In some embodiments, the polypeptide comprising an Fc region is an antibody. In some embodiments, "antibody" is used herein in the broadest sense, and specifically covers monoclonal antibodies (including full length monoclonal antibodies), polyclonal antibodies, multivalent antibodies (e.g., bivalent, trivalent, tetravalent, etc.), and multispecific antibodies (e.g., bispecific, trispecific, etc.). Antibodies may be from any origin, including, for example, humans, non-human primates, rodents (e.g., mouse, rat, hamster, etc.), rabbits, camelids, sharks, and/or recombinantly produced. In some embodiments, the antibody is a human antibody, a humanized antibody, and/or a chimeric antibody. In some embodiments, the antibody is a monoclonal antibody. In some embodiments, the antibody is a multispecific and/or multivalent antibody. In some embodiments, the antibody is a bispecific antibody or a trispecific antibody.

In some embodiments, the sample (e.g., a cell lysate sample, a cell culture supernatant sample, etc.) comprising the polypeptide comprising an Fc region further comprises one of more impurities. In some embodiments, the one or more impurities are present in the sample due to the process employed for producing the polypeptide comprising the Fc region (e.g., the process of producing a secreted antibody). In some embodiments, the one or more impurities are one or more impurities derived from a host cell (e.g., one or more host cell proteins, one or more host cell nucleic acids, one or more host cell lipids, etc.). The host cell may be any host cell known in the art suitable for the production of a polypeptide comprising an Fc region, including, for example, prokaryotic cells (such as *E. coli* cells, *A. niger* cells, etc.), eukaryotic cells (such as yeast cells, plant cells, insect cells (e.g., Si cells), and/or mammalian (mouse, rat, hamster, rabbit, human, non-human primate, etc.) cells (e.g., hybridomas, CHO cells, 293T cells, PER.C6 cells, NS0 cells, etc.). In some embodiments, the one or more impurities are one or more host cell proteins (HCPs). In some embodiments, an HCP refers to a non-product protein produced by a host cell during cell culture or fermentation. In some embodiments, the one or more impurities are one or more (e.g., one or more, two or more, three or more, four or more, etc.) host cell proteins (HCPs) selected from phospholipases, clusterin, serine proteases, elongation factors, and/or any combinations thereof. In some embodiments, the host cell is a CHO cell. In some embodiments, the one or more impurities are one or more CHO cell HCPs. In some embodiments, the one or more CHO cell HCPs are one or more of phospholipases, clusterin, serine proteases, elongation factors, and/or any combinations thereof.

In some embodiments, the present disclosure relates to methods of purifying a polypeptide comprising an Fc region away from one or more impurities in a sample via protein A chromatography. In some embodiments, the sample is contacted with a protein A matrix or resin. In some embodiments, the sample is contacted with the protein A matrix or resin under conditions suitable for the polypeptide comprising the Fc region in the sample to bind to protein A. Methods and suitable conditions for contacting and binding an Fc-region containing polypeptide to a protein A matrix or resin are readily understood by one of ordinary skill in the art (e.g., methods as described in the manufacturer's protocol of a commercially available protein A matrix or resin). Any suitable protein A matrix or resin known in the art may be used in the methods of the present disclosure, including, for example: Mab Select, Mab Select Xtra, Mab Select Sure, Mab Select Sure LX Protein A, Mab Select pcc, Mab Select PrismA, rProtein A Sepharose CL-4B, and nProtein A Sepharose 4 FF (GE Healthcare); EshmunoA, ProSep A, ProSep-vA High Capacity, ProSep-vA Ultra, and ProSep-vA UltraPlus (Millipore); Poros A and Mabcapture A (Poros); IPA-300, IPA-400, and IPA-500 (RepliGen Corp.); Affigel protein A and Affiprep protein A (Bio-Rad); MABsorbent A1PP and MABsorbent A2P (Affinity Chromatography Ltd.); Protein A Ceramic Hyper D F (Pall Corp.); Ultralink Immobilized protein A and Agarose Protein A (PIERCE); Protein A Cellthru 300 and Protein A Ultraflow (Biosepation); Amsphere A3 (JSR); and/or Toyopearl AF-rProtein A HC-650F (Tosoh Biosciences). In some embodiments, the protein A matrix or resin is used in a column chromatography format. In some embodiments, one or more parameters of the protein A matrix or resin (such as pH, ionic strength, temperature, the addition of other substances) is adjusted prior to contacting the protein A matrix or resin with a sample. In some embodiments, the protein A matrix or resin is flushed, washed, equilibrated, stripped, and/or sanitized prior to and/or after contacting the protein A matrix or resin with the sample. In some embodiments, the protein A matrix or resin is equilibrated and/or washed prior to contacting the protein A matrix or resin with the sample. Any suitable equilibration and/or wash buffer known in the art may be used. In some embodiments, the protein A matrix or resin is sanitized, stripped, and/or regenerated between uses.

Washing the Protein a Matrix or Resin with a Wash Solution

Certain aspects of the present disclosure relate to methods of purifying a polypeptide comprising an Fc region via protein A chromatography by washing a protein A matrix or resin bound to the polypeptide comprising an Fc region (e.g., an antibody) with a wash solution comprising a benzoate salt and/or benzyl alcohol. In some embodiments, the method comprises a step of: contacting a protein A chromatography matrix or resin with a sample comprising (1) a polypeptide comprising an Fc region (e.g., an antibody) and (2) one or more impurities (e.g., host cell impurities) under a condition that the polypeptide comprising the Fc region (e.g., the antibody) binds to protein A; and washing the matrix or resin with a wash solution comprising a benzoate salt at a concentration of about 0.1 M to about 1.0 M and/or benzyl alcohol at a concentration of about 0.5% to about 4% volume/volume (v/v), where the wash solution has a pH of about 4.0 to about 10.0. In some embodiments, the wash solution comprises a benzoate salt. In some embodiments, the wash solution comprises benzyl alcohol. In some embodiments, the wash solution comprises a benzoate salt and benzyl alcohol.

In some embodiments, the present disclosure relates to a wash solution comprising a benzoate salt and/or benzoic acid (e.g., pH adjusted). Any suitable source or form of a benzoate salt (e.g., an alkali salt) and/or benzoic acid known in the art may be used in the wash solutions of the present disclosure, including, for example, sodium benzoate, potassium benzoate, lithium benzoate, calcium benzoate, magnesium benzoate, beryllium benzoate, barium benzoate, strontium benzoate, rubidium benzoate, cesium benzoate, and/or any combinations thereof. In some embodiments, the benzoate salt is a benzoate alkali salt. In some embodiments, the benzoate salt is sodium benzoate or potassium benzoate. In some embodiments, the benzoate salt is sodium benzoate.

In some embodiments, the benzoate salt (e.g., sodium benzoate) and/or benzoic acid is present in the wash solution at a concentration of about 0.1 M to about 1.0 M. For example, the benzoate salt (e.g., sodium benzoate) and/or benzoic acid may be present in the wash solution at a concentration of about 0.1 M to about 1.0 M, about 0.1 M to about 0.9 M, about 0.1 M to about 0.8 M, about 0.1 M to about 0.7 M, about 0.1 M to about 0.6 M, about 0.1 M to about 0.5 M, about 0.1 M to about 0.4 M, about 0.1 M to about 0.3 M, about 0.1 M to about 0.2 M, about 0.2 M to about 1.0 M, about 0.2 M to about 0.9 M, about 0.2 M to about 0.8 M, about 0.2 M to about 0.7 M, about 0.2 M to about 0.6 M, about 0.2 M to about 0.5 M, about 0.2 M to about 0.4 M, about 0.2 M to about 0.3 M, about 0.3 M to about 1.0 M, about 0.3 M to about 0.9 M, about 0.3 M to about 0.8 M, about 0.3 M to about 0.7 M, about 0.3 M to about 0.6 M, about 0.3 M to about 0.5 M, about 0.4 M to about 1.0 M, about 0.4 M to about 0.9 M, about 0.4 M to about 0.8 M, about 0.4 M to about 0.7 M, about 0.4 M to about 0.6 M, about 0.5 M to about 1.0 M, about 0.5 M to about 0.9 M, about 0.5 M to about 0.8 M, about 0.5 M to about 0.7 M, about 0.5 M to about 0.6 M, about 0.6 M to about 1.0 M, about 0.6 M to about 0.9 M, about 0.6 M to about 0.8 M, about 0.6 M to about 0.7 M, about 0.7 M to about 1.0 M, about 0.7 M to about 0.9 M, about 0.8 M to about 1.0 M, about 0.8 M to about 0.9 M, or about 0.9 M to about 1.0 M. In some embodiments, the benzoate salt (e.g., sodium benzoate) and/or benzoic acid is present in the wash solution at a concentration of about 0.1 M to about 0.5 M. In some embodiments, the benzoate salt (e.g., sodium benzoate) and or benzoic acid is present in the wash solution at a concentration of about 0.1 M to about 0.3 M.

In some embodiments, the benzoate salt (e.g., sodium benzoate) and/or benzoic acid is present in the wash solution at a concentration of any of about 0.1 M, 0.15 M, 0.2 M, 0.25 M, 0.3 M, 0.35 M, 0.4 M, 0.45 M, 0.5 M, 0.55 M, 0.6 M, 0.65 M, 0.7 M, 0.75 M, 0.8 M, 0.85 M, 0.9 M, 0.95 M, or 1.0 M. In some embodiments, the benzoate salt (e.g., sodium benzoate) and/or benzoic acid is present in the wash solution at a concentration of about 0.5 M. In some embodiments, the benzoate salt (e.g., sodium benzoate) and/or benzoic acid is present in the wash solution at a concentration of about 0.1 M or less than about 0.1 M, about 0.3 M or less than about 0.3 M, about 0.5 M or less than about 0.5 M, about 0.75 M or less than about 0.75 M, or about 1.0 M or less than about 1.0 M. In some embodiments, the benzoate salt (e.g., sodium benzoate) and/or benzoic acid is present in the wash solution at a concentration of about 0.5 M or less than about 0.5 M.

In some embodiments, the present disclosure relates to a wash solution comprising benzyl alcohol. Any suitable source or form of benzyl alcohol known in the art may be used in the wash solutions of the present disclosure.

In some embodiments, the benzyl alcohol is present in the wash solution at a concentration of about 0.5% to about 4.0% volume/volume (v/v). For example, the benzyl alcohol may be present in the wash solution at a concentration of about 0.5% to about 4%, about 1% to about 4%, about 1.5% to about 4%, about 2% to about 4%, about 2.5% to about 4%, about 3% to about 4%, about 3.5% to about 4%, about 0.5% to about 3.5%, about 1% to about 3.5%, about 1.5% to about 3.5%, about 2% to about 3.5%, about 2.5% to about 3.5%, about 3% to about 3.5%, about 0.5% to about 3%, about 1% to about 3%, about 1.5% to about 3%, about 2% to about 3%, about 2.5% to about 3%, about 0.5% to about 2.5%, about 1% to about 2.5%, about 1.5% to about 2.5%, about 2% to about 2.5%, about 0.5% to about 2%, about 1% to about 2%, about 1.5% to about 2%, about 0.5% to about 1.5%, about 1% to about 1.5%, or about 0.5% to about 1% (v/v). In some embodiments, the benzyl alcohol is present in the wash solution at a concentration of about 1% to about 4% volume/volume (v/v). In some embodiments, the benzyl alcohol is present in the wash solution at a concentration of about 1% to about 2% volume/volume (v/v).

In some embodiments, the benzyl alcohol is present in the wash solution at a concentration of any of about 0.5%, 0.75%, 1%, 1.25%, 1.5%, 1.75%, 2%, 2.25%, 2.5%, 2.75%, 3%, 3.25%, 3.5%, 3.75%, or about 4% (v/v). In some embodiments, the benzyl alcohol is present in the wash solution at a concentration of about 2% (v/v). In some embodiments, the benzyl alcohol is present in the wash solution at a concentration of about 1% or less than about 1%, about 2% or less than about 2%, about 3% or less than about 3%, or about 4% or less than about 4%. In some embodiments, the benzyl alcohol is present in the wash solution at a concentration of about 4% or less than about 4% (v/v). In some embodiments, the benzyl alcohol is present in the wash solution at a concentration of about 4% or less than about 2% (v/v).

Additives

In some embodiments, a wash solution of the present disclosure further comprises one or more (e.g., one or more, two or more, three or more, four or more, or all five) of the following additives: benzenesulfonate, caprylic acid, hexylene glycol, a non-buffering salt, and/or creatine at any of the concentrations described herein. In some embodiments, the wash solution comprising the one or more additives has a pH of about 4.0 to about 10.0. In some embodiments, the inclusion of the one or more additives in the wash solution further improves the purification of a polypeptide comprising an Fc region away from one or more impurities (e.g., host cell impurities) by the methods described herein.

In some embodiments, the wash solution comprises a benzoate salt and/or benzyl alcohol and one of benzenesulfonate, caprylic acid, hexylene glycol, a non-buffering salt, and/or creatine at a pH of about 4.0 to about 10.0. For example, the wash solution may comprise: benzoate salt and/or benzyl alcohol and benzenesulfonate; benzoate salt and/or benzyl alcohol and caprylic acid; benzoate salt and/or benzyl alcohol and hexylene glycol; benzoate salt and/or benzyl alcohol and a non-buffering salt; or benzoate salt and/or benzyl alcohol and creatine, at a pH of about 4.0 to about 10.0.

In some embodiments, the wash solution comprises a benzoate salt and/or benzyl alcohol and two of benzenesulfonate, caprylic acid, hexylene glycol, a non-buffering salt, and/or creatine at a pH of about 4.0 to about 10.0. For example, the wash solution may comprise: benzoate salt and/or benzyl alcohol, benzenesulfonate, and caprylic acid; benzoate salt and/or benzyl alcohol, benzenesulfonate, and hexylene glycol; benzoate salt and/or benzyl alcohol, benzenesulfonate, and a non-buffering salt; benzoate salt and/or benzyl alcohol, benzenesulfonate, and creatine; benzoate salt and/or benzyl alcohol, caprylic acid, and hexylene glycol; benzoate salt and/or benzyl alcohol, caprylic acid, and a non-buffering salt; benzoate salt and/or benzyl alcohol, caprylic acid, and creatine; benzoate salt and/or benzyl alcohol, hexylene glycol, and a non-buffering salt; benzoate salt and/or benzyl alcohol, hexylene glycol, and creatine; or benzoate salt and/or benzyl alcohol, a non-buffering salt, and creatine, at a pH of about 4.0 to about 10.0.

In some embodiments, the wash solution comprises a benzoate salt and/or benzyl alcohol and three of benzenesulfonate, caprylic acid, hexylene glycol, a non-buffering salt, and/or creatine at a pH of about 4.0 to about 10.0. For example, the wash solution may comprise: benzoate salt and/or benzyl alcohol, benzenesulfonate, caprylic acid, and hexylene glycol; benzoate salt and/or benzyl alcohol, benzenesulfonate, caprylic acid, and a non-buffering salt; benzoate salt and/or benzyl alcohol, benzenesulfonate, caprylic acid, and creatine; benzoate salt and/or benzyl alcohol, benzenesulfonate, hexylene glycol, and a non-buffering salt; benzoate salt and/or benzyl alcohol, benzenesulfonate, hexylene glycol, and creatine; benzoate salt and/or benzyl alcohol, benzenesulfonate, a non-buffering salt, and creatine; benzoate salt and/or benzyl alcohol, caprylic acid, hexylene glycol, and a non-buffering salt; benzoate salt and/or benzyl alcohol, caprylic acid, hexylene glycol, and creatine; or benzoate salt and/or benzyl alcohol, caprylic acid, a non-buffering salt, and creatine; benzoate salt and/or benzyl alcohol, hexylene glycol, a non-buffering salt, and creatine, at a pH of about 4.0 to about 10.0.

In some embodiments, the wash solution comprises a benzoate salt and/or benzyl alcohol and four of benzenesulfonate, caprylic acid, hexylene glycol, a non-buffering salt, and/or creatine at a pH of about 4.0 to about 10.0. For example, the wash solution may comprise: benzoate salt and/or benzyl alcohol, benzenesulfonate, caprylic acid, hexylene glycol, and a non-buffering salt; benzoate salt and/or benzyl alcohol, benzenesulfonate, caprylic acid, hexylene glycol, and creatine; benzoate salt and/or benzyl alcohol, benzenesulfonate, caprylic acid, a non-buffering salt, and creatine; benzoate salt and/or benzyl alcohol, benzenesulfonate, hexylene glycol, a non-buffering salt, and creatine; or benzoate salt and/or benzyl alcohol, caprylic acid, hexylene glycol, a non-buffering salt, and creatine, at a pH of about 4.0 to about 10.0.

In some embodiments, the wash solution comprises a benzoate salt and/or benzyl alcohol and all five of benzenesulfonate, caprylic acid, hexylene glycol, a non-buffering salt, and creatine at a pH of about 4.0 to about 10.0.

In some embodiments, the present disclosure relates to a wash solution comprising benzenesulfonate. Any suitable form or source of benzenesulfonate known in the art may be used in the wash solutions of the present disclosure, including, for example, a benzenesulfonate salt (e.g., an alkali salt) such as sodium benzenesulfonate or potassium benzenesulfonate, benzenesulfonic acid, and/or any combinations thereof. In some embodiments, the benzenesulfonate is sodium benzenesulfonate.

In some embodiments, the benzenesulfonate (e.g., sodium benzenesulfonate) is present in the wash solution at a concentration of about 0.1 M to about 0.5 M. For example, the sodium benzenesulfonate may be present in the wash solution at a concentration of about 0.1 M to about 0.5 M, about 0.1 M to about 0.4 M, about 0.1 M to about 0.3 M, about 0.1 M to about 0.2 M, about 0.2 M to about 0.5 M, about 0.2 M to about 0.4 M, about 0.2 M to about 0.3 M, about 0.3 M to about 0.5 M, about 0.3 M to about 0.4 M, or about 0.4 M to about 0.5 M. In some embodiments, the sodium benzenesulfonate is present in the wash solution at a concentration of about 0.1 M to about 0.3 M.

In some embodiments, the sodium benzenesulfonate is present in the wash solution at a concentration of any of about 0.1 M, 0.15 M, 0.2 M, 0.25 M, 0.3 M, 0.35 M, 0.4 M, 0.45 M, or 0.5 M. In some embodiments, the sodium benzenesulfonate is present in the wash solution at a concentration of about 0.5 M. In some embodiments, the sodium benzenesulfonate is present in the wash solution at a concentration of about 0.1 M or less than about 0.1 M, about 0.3 M or less than about 0.3 M, or about 0.5 M or less than about 0.5 M. In some embodiments, the sodium benzenesulfonate is present in the wash solution at a concentration of about 0.5 M or less than about 0.5 M.

In some embodiments, the present disclosure relates to a wash solution comprising caprylic acid. Any suitable form or source of caprylic acid known in the art may be used in the wash solutions of the present disclosure.

In some embodiments, the caprylic acid is present in the wash solution at a concentration of about 1 mM to about 50 mM. For example, the caprylic acid may be present in the wash solution at a concentration of about 1 mM to about 50 mM, about 10 mM to about 50 mM, about 20 mM to about 50 mM, about 30 mM to about 50 mM, about 40 mM to about 50 mM, about 1 mM to about 40 mM, about 10 mM to about 40 mM, about 20 mM to about 40 mM, about 30 mM to about 40 mM, about 1 mM to about 30 mM, about 10 mM to about 30 mM, about 20 mM to about 30 mM, about 1 mM to about 20 mM, about 10 mM to about 20 mM, or about 1 mM to about 10 mM. In some embodiments, the caprylic acid is present in the wash solution at a concentration of about 10 mM to about 50 mM.

In some embodiments, the caprylic acid is present in the wash solution at a concentration of any of about 1 mM, 5 mM, 10 mM, 15 mM, 20 mM, 25 mM, 30 mM, 35 mM, 40 mM, 45 mM, or 50 mM. In some embodiments, the caprylic acid is present in the wash solution at a concentration of about 50 mM. In some embodiments, the caprylic acid is present in the wash solution at a concentration of about 10 mM or less than about 10 mM, about 30 mM or less than about 30 mM, or about 50 mM or less than about 50 mM. In some embodiments, the caprylic acid is present in the wash solution at a concentration of about 50 mM or less than about 50 mM.

In some embodiments, the present disclosure relates to a wash solution comprising hexylene glycol. Any suitable form or source of hexylene glycol known in the art may be used in the wash solutions of the present disclosure.

In some embodiments, the hexylene glycol is present in the wash solution at a concentration of about 0.5% to about 10% (v/v). For example, the hexylene may be present in the wash solution at a concentration of about 0.5% to about 10%, about 1% to about 10%, about 2% to about 10%, about 4% to about 10%, about 6% to about 10%, about 8% to about 10%, about 9% to about 10%, 0.5% to about 9%, about 1% to about 9%, about 2% to about 9%, about 4% to about 9%, about 6% to about 9%, about 8% to about 9%, about 0.5% to about 8%, about 1% to about 8%, about 2% to about 8%, about 4% to about 8%, about 6% to about 8%, about 0.5% to about 6%, about 1% to about 6%, about 2% to about 6%, about 4% to about 6%, about 0.5% to about 4%, about 1% to about 4%, about 2% to about 4%, about 0.5% to about 2%, about 1% to about 2%, or about 0.5% to about 1% (v/v). In some embodiments, the hexylene glycol is present in the wash solution at a concentration of about 1% to about 10% (v/v).

In some embodiments, the hexylene glycol is present in the wash solution at a concentration of any of about 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10% (v/v). In some embodiments, the hexylene glycol is present in the wash solution at a concentration of about 10% (v/v). In some embodiments, the hexylene glycol is present in the wash solution at a concentration of about 1% or less than about 1%, about 2% or less than about 2%, about 4% or less than about 4%, about 6% or less than about 6%, about 8% or less than about 8%, or about 10% or less than about 10% (v/v). In some embodiments, the hexylene glycol is present in the wash solution at a concentration of about 10% or less than about 10% (v/v).

In some embodiments, the present disclosure relates to a wash solution comprising one or more (e.g., one or, two or more, three or more, etc.) non-buffering salts. Any suitable form or source of a non-buffering salt known in the art may be used in the wash solutions of the present disclosure. Non-buffering salts may include halogen salts (such as those that comprise Cl or Br), in particular halogen salts comprising alkali metals (such as Na or K) or alkaline earth metals (such as Ca or Mg). In some embodiments, the non-buffering salt is sodium chloride or potassium chloride. In some embodiments, the non-buffering salt is sodium chloride.

In some embodiments, the non-buffering salt (e.g., sodium chloride) is present in the wash solution at a concentration of about 0.1 M to about 1.0 M. For example, the non-buffering salt (e.g., sodium chloride) may be present in the wash solution at a concentration of about 0.1 M to about 1.0 M, about 0.1 M to about 0.8 M, about 0.1 M to about 0.6 M, about 0.1 M to about 0.5 M, about 0.1 M to about 0.4 M, about 0.1 M to about 0.2 M, about 0.2 M to about 1.0 M, about 0.2 M to about 0.8 M, about 0.2 M to about 0.6 M, about 0.2 M to about 0.5 M, about 0.2 M to about 0.4 M, about 0.4 M to about 1.0 M, about 0.4 M to about 0.8 M, about 0.4 M to about 0.6 M, about 0.4 M to about 0.5 M, about 0.5 M to about 1.0 M, about 0.5 M to about 0.8 M, about 0.5 M to about 0.6 M, about 0.6 M to about 1.0 M, about 0.6 M to about 0.8 M, or about 0.8 M to about 1.0 M. In some embodiments, the non-buffering salt (e.g., sodium chloride) is present in the wash solution at a concentration of about 0.1 M to about 0.5 M. In some embodiments, the non-buffering salt (e.g., sodium chloride) is present in the wash solution at a concentration of about 0.5 M to about 1.0 M.

In some embodiments, the non-buffering salt (e.g., sodium chloride) is present in the wash solution at a concentration of any of about 0.1 M, 0.15 M, 0.2 M, 0.25 M, 0.3 M, 0.35 M, 0.4 M, 0.45 M, 0.5 M, 0.55 M, 0.6 M, 0.65 M, 0.7 M, 0.75 M, 0.8 M, 0.85 M, 0.9 M, 0.95 M, or 1.0 M. In some embodiments, the non-buffering salt (e.g., sodium chloride) is present in the wash solution at a concentration of about 0.5 M. In some embodiments, the non-buffering salt (e.g., sodium chloride) is present in the wash solution at a concentration of about 1.0 M. In some embodiments, the non-buffering salt (e.g., sodium chloride) is present in the wash solution at a concentration of about 0.1 M or less than about 0.1 M, about 0.2 M or less than about 0.2 M, about 0.4 M or less than about 0.4 M, about 0.5 M or less than about 0.5 M, about 0.6 M or less than about 0.6 M, about 0.8 M or less than about 0.8 M, or about 1.0 M or less than about 1.0 M. In some embodiments, the non-buffering salt (e.g., sodium chloride) is present in the wash solution at a concentration of about 0.5 M or less than about 0.5 M. In some embodiments, the non-buffering salt (e.g., sodium chloride) is present in the wash solution at a concentration of about 1.0 M or less than about 1.0 M.

In some embodiments, the present disclosure relates to a wash solution comprising creatine. Any suitable form or source of creatine known in the art may be used in the wash solutions of the present disclosure, including, for example, creatine-HCl, creatine esters, creatine pyruvate, creatine phosphate, create alpha-ketoglutarate, creatine citrate, and/or any combinations thereof. In some embodiments, the creatine is creatine-HCl.

In some embodiments, the creatine is present in the wash solution at a concentration of about 1 mM to about 100 mM. For example, the creatine may be present in the wash solution at a concentration of about 1 mM to about 100 mM, about 10 mM to about 100 mM, about 25 mM to about 100 mM, about 50 mM to about 100 mM, about 75 mM to about 100 mM, about 1 mM to about 75 mM, about 10 mM to about 75 mM, about 25 mM to about 75 mM, about 50 mM to about 75 mM, about 1 mM to about 50 mM, about 10 mM to about 50 mM, about 25 mM to about 50 mM, about 1 mM to about 25 mM, about 10 mM to about 25 mM, or about 1 mM to about 10 mM. In some embodiments, the creatine is present in the wash solution at a concentration of about 10 mM to about 100 mM. In some embodiments, the creatine is present in the wash solution at a concentration of about 10 mM to about 50 mM. In some embodiments, the creatine is present in the wash solution at a concentration of any of about 1 mM, 5 mM, 10 mM, 15 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM, or 100 mM. In some embodiments, the creatine is present in the wash solution at a concentration of about 50 mM.

Arginine

In some embodiments, the present disclosure relates to a wash solution further comprising arginine and/or an arginine derivative. In some embodiments, the inclusion of arginine and/or an arginine derivative in the wash solution further improves the purification of a polypeptide comprising an Fc region away from one or more impurities (e.g., host cell impurities) by the methods described herein. Any suitable form or source of arginine and/or an arginine derivative known in the art may be used in the wash solutions of the present disclosure, including, for example, arginine, arginine-HCl, acetyl arginine, agmatine, arginic acid, N-alpha-butyroyl-L-arginine, N-alpha-pyvaloyl arginine, and/or any combinations thereof. The arginine and/or arginine derivative may be L-arginine and/or D-arginine, and derivatives thereof. In some embodiments, the arginine and/or arginine derivative is arginine-HCl.

In some embodiments, the present disclosure relates to the use of arginine and/or an arginine derivative (e.g., arginine-HCl) in a wash solution comprising a benzoate salt and/or benzyl alcohol. In some embodiments, the wash solution comprises a benzoate salt and arginine and/or an arginine derivative (e.g., arginine-HCl). In some embodiments, the wash solution comprises benzyl alcohol and arginine and/or an arginine derivative (e.g., arginine-HCl). In some embodiments, the wash solution comprises a benzoate salt, benzyl alcohol, and arginine and/or an arginine derivative (e.g., arginine-HCl). In some embodiments, the wash solution further comprises one or more (e.g., one or more, two or more, three or more, four or more, or all five) of benzenesulfonate, caprylic acid, hexylene glycol, a non-buffering salt, and/or creatine at any of the concentrations described herein. In some embodiments, a wash solution comprising arginine and/or an arginine derivative has a pH of about 4.0 to about 10.0. In some embodiments, a wash solution comprising arginine and/or an arginine derivative has a pH of about 4.0 to about 6.0. In some embodiments, a wash solution comprising arginine and/or an arginine derivative has a pH of about 4.0 to about 5.0. In some embodiments, a wash solution comprising arginine and/or an arginine derivative has a pH of about 8.0 to about 10.0. In some embodiments, a wash solution comprising arginine and/or an arginine derivative has a pH of about 8.0 to about 9.0.

In some embodiments, the wash solution comprises a benzoate salt and/or benzyl alcohol, arginine and/or an arginine derivative (e.g., arginine-HCl), and one of benzenesulfonate, caprylic acid, hexylene glycol, a non-buffering salt, and/or creatine. For example, the wash solution may comprise: benzoate salt and/or benzyl alcohol, arginine, and benzenesulfonate; benzoate salt and/or benzyl alcohol, arginine, and caprylic acid; benzoate salt and/or benzyl alcohol, arginine, and hexylene glycol; benzoate salt and/or benzyl alcohol, arginine, and a non-buffering salt; or benzoate salt and/or benzyl alcohol, arginine, and creatine.

In some embodiments, the wash solution comprises a benzoate salt and/or benzyl alcohol, arginine and/or an arginine derivative (e.g., arginine-HCl), and two of benzenesulfonate, caprylic acid, hexylene glycol, a non-buffering salt, and/or creatine. For example, the wash solution may comprise: benzoate salt and/or benzyl alcohol, arginine, benzenesulfonate, and caprylic acid; benzoate salt and/or benzyl alcohol, arginine, benzenesulfonate, and hexylene glycol; benzoate salt and/or benzyl alcohol, arginine, benzenesulfonate, and a non-buffering salt; benzoate salt and/or benzyl alcohol, arginine, benzenesulfonate, and creatine; benzoate salt and/or benzyl alcohol, arginine, caprylic acid, and hexylene glycol; benzoate salt and/or benzyl alcohol, arginine, caprylic acid, and a non-buffering salt; benzoate salt and/or benzyl alcohol, arginine, caprylic acid, and creatine; benzoate salt and/or benzyl alcohol, arginine, hexylene glycol, and a non-buffering salt; benzoate salt and/or benzyl alcohol, arginine, hexylene glycol, and creatine; or benzoate salt and/or benzyl alcohol, arginine, a non-buffering salt, and creatine.

In some embodiments, the wash solution comprises a benzoate salt and/or benzyl alcohol, arginine and/or an arginine derivative (e.g., arginine-HCl), and three of benzenesulfonate, caprylic acid, hexylene glycol, a non-buffering salt, and/or creatine. For example, the wash solution may comprise: benzoate salt and/or benzyl alcohol, arginine, benzenesulfonate, caprylic acid, and hexylene glycol; benzoate salt and/or benzyl alcohol, arginine, benzenesulfonate, caprylic acid, and a non-buffering salt; benzoate salt and/or benzyl alcohol, arginine, benzenesulfonate, caprylic acid, and creatine; benzoate salt and/or benzyl alcohol, arginine, benzenesulfonate, hexylene glycol, and a non-buffering salt; benzoate salt and/or benzyl alcohol, arginine, benzenesulfonate, hexylene glycol, and creatine; benzoate salt and/or benzyl alcohol, arginine, benzenesulfonate, a non-buffering salt, and creatine; benzoate salt and/or benzyl alcohol, arginine, caprylic acid, hexylene glycol, and a non-buffering salt; benzoate salt and/or benzyl alcohol, arginine, caprylic acid, hexylene glycol, and creatine; benzoate salt and/or benzyl alcohol, arginine, caprylic acid, a non-buffering salt, and creatine; or benzoate salt and/or benzyl alcohol, arginine, hexylene glycol, a non-buffering salt, and creatine.

In some embodiments, the wash solution comprises a benzoate salt and/or benzyl alcohol, arginine and/or an arginine derivative (e.g., arginine-HCl), and four of benzenesulfonate, caprylic acid, hexylene glycol, a non-buffering salt, and/or creatine. For example, the wash solution may comprise: benzoate salt and/or benzyl alcohol, arginine, benzenesulfonate, caprylic acid, hexylene glycol, and a non-buffering salt; benzoate salt and/or benzyl alcohol, arginine, benzenesulfonate, caprylic acid, hexylene glycol, and creatine; benzoate salt and/or benzyl alcohol, arginine, benzenesulfonate, caprylic acid, a non-buffering salt, and creatine; benzoate salt and/or benzyl alcohol, arginine, benzenesulfonate, hexylene glycol, a non-buffering salt, and creatine; benzoate salt and/or benzyl alcohol, arginine, caprylic acid, hexylene glycol, a non-buffering salt, and creatine.

In some embodiments, the wash solution comprises a benzoate salt and/or benzyl alcohol, arginine and/or an arginine derivative (e.g., arginine-HCl), and all five of benzenesulfonate, caprylic acid, hexylene glycol, a non-buffering salt, and creatine.

In some embodiments, the arginine and/or arginine derivative (e.g., arginine-HCl) is present in the wash solution at a concentration of about 0.1 M to about 1.0 M. For example, the arginine and/or arginine derivative (e.g., arginine-HCl) may be present in the wash solution at a concentration of about 0.1 M to about 1.0 M, about 0.1 M to about 0.9 M, about 0.1 M to about 0.8 M, about 0.1 M to about 0.7 M, about 0.1 M to about 0.6 M, about 0.1 M to about 0.5 M, about 0.1 M to about 0.4 M, about 0.1 M to about 0.3 M, about 0.1 M to about 0.2 M, about 0.2 M to about 1.0 M, about 0.2 M to about 0.9 M, about 0.2 M to about 0.8 M, about 0.2 M to about 0.7 M, about 0.2 M to about 0.6 M, about 0.2 M to about 0.5 M, about 0.2 M to about 0.4 M, about 0.2 M to about 0.3 M, about 0.3 M to about 1.0 M, about 0.3 M to about 0.9 M, about 0.3 M to about 0.8 M, about 0.3 M to about 0.7 M, about 0.3 M to about 0.6 M, about 0.3 M to about 0.5 M, about 0.3 M to about 0.4 M, about 0.4 M to about 1.0 M, about 0.4 M to about 0.9 M, about 0.4 M to about 0.8 M, about 0.4 M to about 0.7 M, about 0.4 M to about 0.6 M, about 0.4 M to about 0.5 M, about 0.5 M to about 1.0 M, about 0.5 M to about 0.9 M, about 0.5 M to about 0.8 M, about 0.5 M to about 0.7 M, about 0.5 M to about 0.6 M, about 0.6 M to about 1.0 M, about 0.6 M to about 0.9 M, about 0.6 M to about 0.8 M, about 0.6 M to about 0.7 M, about 0.7 M to about 1.0 M, about 0.7 M to about 0.9 M, about 0.7 M to about 0.8 M, about 0.8 M to about 1.0 M, about 0.8 M to about 0.9 M, or about 0.9 M to about 1.0 M. In some embodiments, the arginine and/or arginine derivative (e.g., arginine-HCl) is present in the wash solution at a concentration of about 0.1 M to about 0.5 M. In some embodiments, the arginine and/or arginine derivative (e.g., arginine-HCl) is present in the wash solution at a concentration of about 0.1 M to about 0.3 M.

In some embodiments, the arginine and/or arginine derivative (e.g., arginine-HCl) is present in the wash solution at a concentration of any of about 0.1 M, 0.15 M, 0.2 M, 0.25 M, 0.3 M, 0.35 M, 0.4 M, 0.45 M, 0.5 M, 0.55 M, 0.6 M, 0.65 M, 0.7 M, 0.75 M, 0.8 M, 0.85 M, 0.9 M, 0.95 M, or 1.0 M. In some embodiments, the arginine and/or arginine derivative (e.g., arginine-HCl) is present in the wash solution at a concentration of about 0.5 M. In some embodiments, the arginine and/or arginine derivative (e.g., arginine-HCl) is present in the wash solution at a concentration of about 0.1 M or less than about 0.1 M, about 0.2 M or less than about 0.2 M, about 0.3 M or less than about 0.3 M, about 0.4 M or less than about 0.4 M, about 0.5 M or less than about 0.5 M, about 0.75 M or less than about 0.75 M, or about 1.0 M or less than about 1.0 M. In some embodiments, the arginine and/or arginine derivative (e.g., arginine-HCl) is present in the wash solution at a concentration of about 0.5 M or less than about 0.5 M.

pH

In some embodiments, the present disclosure relates to a wash solution having a pH of about 4.0 to about 10.0. For example, the wash solution may have a pH of about 4.0 to about 10.0, about 5.0 to about 10.0, about 6.0 to about 10.0, about 6.5 to about 10.0, about 7.0 to about 10.0, about 7.5 to about 10.0, about 8.0 to about 10.0, about 9.0 to about 10.0, 4.0 to about 9.0, about 5.0 to about 9.0, about 6.0 to about 9.0, about 6.5 to about 9.0, about 7.0 to about 9.0, about 7.5 to about 9.0, about 8.0 to about 9.0, 4.0 to about 8.0, about 5.0 to about 8.0, about 6.0 to about 8.0, about 6.5 to about 8.0, about 7.0 to about 8.0, about 7.5 to about 8.0, 4.0 to about 7.5, about 5.0 to about 7.5, about 6.0 to about 7.5, about 6.5 to about 7.5, about 7.0 to about 7.5, about 4.0 to about 7.0, about 5.0 to about 7.0, about 6.0 to about 7.0, about 6.5 to about 7.0, 4.0 to about 6.5, about 5.0 to about 6.5, about 6.0 to about 6.5, 4.0 to about 6.0, about 5.0 to about 6.0, or about 4.0 to about 5.0. In some embodiments, the wash solution has a pH of about 5.0 to about 9.0. In some embodiments, the wash solution has a pH of about 4.0 to about 6.0. In some embodiments, the wash solution has a pH of about 4.0 to about 5.0. In some embodiments, the wash solution has a pH of about 8.0 to about 10.0. In some embodiments, the wash solution has a pH of about 8.0 to about 9.0.

In some embodiments, the wash solution has a pH of any of about 4.0, 4.25, 4.5, 4.75, 5.0, 5.25, 5.5, 5.75, 6.0, 6.25, 6.5, 6.75, 7.0, 7.25, 7.5, 7.75, 8.0, 8.25, 8.5, 8.75, 9.0, 9.25, 9.5, 9.75, or 10.0. In some embodiments, the wash solution has a pH of about 4.0. In some embodiments, the wash solution has a pH of about 5.0. In some embodiments, the wash solution has a pH of about 6.0. In some embodiments, the wash solution has a pH of about 6.5. In some embodiments, the wash solution has a pH of about 7.0. In some embodiments, the wash solution has a pH of about 7.5. In some embodiments, the wash solution has a pH of about 9.0. In some embodiments, the wash solution has a pH of about 10.0.

Buffering Agent

In some embodiments, a wash solution of the present disclosure further comprises one or more (e.g., one or more, two or more, three or more, four or more, five or more, etc.) buffering agents. Any suitable buffering agent known in the art may be used in the wash solutions of the present disclosure, including, for example phosphate, tris (tris(hydroxymethyl)methylamine), bis-tris, bis-tris propane, arginine, histidine, triethanolamine, diethanolamine, formate, acetate, carbonate MES (2-(N-mopholino)ethanesulfonic acid), citrate, HEPES (4-2-hydroxyethyl-1-piperazineethanesulfonic acid), MOPS (3-(N-morpholino) propanesulfonic acid), TAPS (3-{[tris(hydroxymehtyl)methyl]amino}propanesulfonic acid), Bicine (N,N-bis(2-hydroxyethyl)glycine), Tricine (N-tris(hydroxymethyl)methylglycine), TES (2-{[tris(hydroxymethyl)methyl]amino}ethanesulfonic acid), PIPES (piperazine-N,N'-bis(2-ethanesulfonic acid), cacodylae (dimethylarsinic acid), SSC (saline sodium citrate), and/or any combinations thereof. In some embodiments, the buffering agent is one or more of phosphate, tris, arginine, acetate, and/or citrate.

In some embodiments, the buffering agent (e.g., phosphate, tris, arginine, acetate, and/or citrate) is present in the wash solution at a concentration of about 1 mM to about 100 mM or about 1 mM to about 500 mM. For example, the buffering agent (e.g., phosphate, tris, arginine, acetate, and/or citrate) may be present in the wash solution at a concentration of about 1 mM to about 500 mM, 10 mM to about 500 mM, 50 mM to about 500 mM, 100 mM to about 500 mM, 150 mM to about 500 mM, 200 mM to about 500 mM, 250 mM to about 500 mM, 300 mM to about 500 mM, 350 mM to about 500 mM, 400 mM to about 500 mM, 450 mM to about 500 mM, 1 mM to about 450 mM, 1 mM to about 400 mM, 1 mM to about 350 mM, 1 mM to about 300 mM, 1 mM to about 250 mM, 1 mM to about 200 mM, 1 mM to about 150 mM, 1 mM to about 100 mM, about 10 mM to about 100 mM, about 25 mM to about 100 mM, about 40 mM to about 100 mM, about 50 mM to about 100 mM, about 60 mM to about 100 mM, about 75 mM to about 100 mM, about 1 mM to about 75 mM, about 10 mM to about 75 mM, about 40 mM to about 75 mM, about 50 mM to about 75 mM, about 60 mM to about 75 mM, about 1 mM to about 60 mM, about 10 mM to about 60 mM, about 25 mM to about 60 mM, about 40 mM to about 60 mM, about 50 mM to about 60 mM, about 1 mM to about 50 mM, about 10 mM to about 50 mM, about 25 mM to about 50 mM, about 40 mM to about 50 mM, about 1 mM to about 40 mM, about 10 mM to about 40 mM, about 25 mM to about 40 mM, about 1 mM to about 25 mM, about 10 mM to about 25 mM, or about 1 mM to about 10 mM. In some embodiments, the buffering agent (e.g., phosphate, tris, arginine, acetate, and/or citrate) is present in the wash solution at a concentration of about 10 mM to about 50 mM or about 10 mM to about 500 mM.

In some embodiments, the buffering agent (e.g., phosphate, tris, arginine, acetate, and/or citrate) is present in the wash solution at a concentration of any of about 1 mM, 5 mM, 10 mM, 15 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM, or 100 mM. Alternatively, the buffering agent (e.g., phosphate, tris, arginine, acetate, and/or citrate) is present in the wash solution at a concentration of any of about 150 mM, 200 mM, 250 mM, 300 mM, 350 mM, 400 mM, 450 mM, or 500 mM. In some embodiments, the buffering agent (e.g., phosphate, tris, arginine, acetate, and/or citrate) is present in the wash solution at a concentration of about 500 mM. In some embodiments, the buffering agent (e.g., phosphate, tris, arginine, acetate, and/or citrate) is present in the wash solution at a concentration of about 50 mM. In some embodiments, the buffering agent (e.g., phosphate, tris, arginine, acetate, and/or citrate) is present in the wash solution at a concentration of about 10 mM or less than about 10 mM, about 25 mM or less than about 25 mM, about 50 mM or less than about 50 mM, about 75 mM or less than about 75 mM, or about 100 mM or less than about 100 mM, or about 500 mM or less than about 500 mM. In some embodiments, the buffering agent (e.g., phosphate, tris, arginine, acetate, and/or citrate) is present in the wash solution at a concentration of about 50 mM or less than about 50 mM. In some embodiments, the buffering agent (e.g., phosphate, tris, arginine, acetate, and/or citrate) is present in the wash solution at a concentration of about 500 mM or less than about 500 mM.

Exemplary Wash Solutions

In some embodiments, a wash solution of the present disclosure comprises sodium benzoate and/or benzyl alcohol, and has a pH of about 7.0. In some embodiments, the wash solution comprises sodium benzoate at a concentration of about 0.5 M and/or benzyl alcohol at a concentration of about 2% (v/v), and has a pH of about 7.0. In some embodiments, the wash solution comprises sodium benzoate at a concentration of about 0.5 M and benzyl alcohol at a concentration of about 2% (v/v), and has a pH of about 7.0. In some embodiments, the wash solution further comprises phosphate buffer (e.g., at a concentration of about 50 mM).

In some embodiments, a wash solution of the present disclosure comprises sodium benzoate, benzyl alcohol, and/or sodium chloride, and has a pH of about 7.0. In some embodiments, the wash solution comprises sodium benzoate at a concentration of about 0.5 M, benzyl alcohol at a concentration of about 2% (v/v), and/or sodium chloride at a concentration of about 0.5 M, and has a pH of about 7.0. In some embodiments, the wash solution comprises sodium benzoate at a concentration of about 0.5 M, benzyl alcohol at a concentration of about 2% (v/v), and sodium chloride at a concentration of about 0.5 M, and has a pH of about 7.0. In some embodiments, the wash solution further comprises phosphate buffer (e.g., at a concentration of about 50 mM).

In some embodiments, a wash solution of the present disclosure comprises sodium benzoate, benzyl alcohol, arginine, and/or sodium chloride, and has a pH of about 7.0. In some embodiments, the wash solution comprises sodium benzoate at a concentration of about 0.5 M, benzyl alcohol at a concentration of about 2% (v/v), arginine at a concentration of about 0.5 M, and/or sodium chloride at a concentration of about 0.5 M, and has a pH of about 7.0. In some embodiments, the wash solution comprises sodium benzoate at a concentration of about 0.5 M, benzyl alcohol at a concentration of about 2% (v/v), arginine at a concentration of about 0.5 M, and sodium chloride at a concentration of about 0.5 M, and has a pH of about 7.0. In some embodiments, the wash solution further comprises phosphate buffer (e.g., at a concentration of about 50 mM).

In some embodiments, a wash solution of the present disclosure comprises sodium benzoate, benzyl alcohol, phosphate buffer, and/or arginine, and has a pH of about 9.0. In some embodiments, the wash solution comprises sodium benzoate at a concentration of about 0.5 M, benzyl alcohol at a concentration of about 2% (v/v), phosphate buffer at a concentration of about 50 mM, and/or arginine at a concentration of about 0.5 M, and has a pH of about 9.0. In some embodiments, the wash solution comprises sodium benzoate at a concentration of about 0.5 M, benzyl alcohol at a concentration of about 2% (v/v), phosphate buffer at a concentration of about 50 mM, and arginine at a concentration of about 0.5 M, and has a pH of about 9.0.

In some embodiments, a wash solution of the present disclosure comprises sodium benzoate, benzyl alcohol, and/or arginine, and has a pH of about 6.0. In some embodiments, the wash solution comprises sodium benzoate at a concentration of about 0.5 M, benzyl alcohol at a concentration of about 2% (v/v), and/or arginine at a concentration of about 0.5 M, and has a pH of about 6.0. In some embodiments, the wash solution comprises sodium benzoate at a concentration of about 0.5 M, benzyl alcohol at a concentration of about 2% (v/v), and arginine at a concentration of about 0.5 M, and has a pH of about 6.0.

In some embodiments, a wash solution of the present disclosure comprises hexylene glycol, sodium benzoate, and/or benzyl alcohol, and has a pH of about 7.0. In some embodiments, the wash solution comprises hexylene glycol at a concentration of about 10% (v/v), sodium benzoate at a concentration of about 0.5 M, and/or benzyl alcohol at a concentration of about 2% (v/v), and has a pH of about 7.0. In some embodiments, the wash solution comprises hexylene glycol at a concentration of about 10% (v/v), sodium benzoate at a concentration of about 0.5 M, and benzyl alcohol at a concentration of about 2% (v/v), and has a pH of about 7.0.

In some embodiments, a wash solution of the present disclosure comprises benzenesulfonate, sodium benzoate, and/or benzyl alcohol, and has a pH of about 7.0. In some embodiments, the wash solution comprises benzenesulfonate at a concentration of about 0.5 M, sodium benzoate at a concentration of about 0.5 M, and/or benzyl alcohol at a concentration of about 2% (v/v), and has a pH of about 7.0. In some embodiments, the wash solution comprises benzenesulfonate at a concentration of about 0.5 M, sodium benzoate at a concentration of about 0.5 M, and benzyl alcohol at a concentration of about 2% (v/v), and has a pH of about 7.0.

In some embodiments, a wash solution of the present disclosure comprises sodium benzoate, benzyl alcohol, and/or arginine (e.g., arginine-HCl), and has a pH of about 5.0. In some embodiments, the wash solution comprises sodium benzoate at a concentration of about 0.5 M, benzyl alcohol at a concentration of about 2% (v/v), and/or arginine (e.g., arginine-HCl) at a concentration of about 0.5 M, has a pH of about 5.0. In some embodiments, the wash solution comprises sodium benzoate at a concentration of about 0.5 M, benzyl alcohol at a concentration of about 2% (v/v), and arginine (e.g., arginine-HCl) at a concentration of about 0.5 M, has a pH of about 5.0.

In some embodiments, a wash solution of the present disclosure comprises sodium benzoate, benzyl alcohol, and/or arginine (e.g., arginine-HCl), and has a pH of about 6.0. In some embodiments, the wash solution comprises sodium benzoate at a concentration of about 0.5 M, benzyl alcohol at a concentration of about 2% (v/v), and/or arginine (e.g., arginine-HCl) at a concentration of about 0.5 M, has a pH of about 6.0. In some embodiments, the wash solution comprises sodium benzoate at a concentration of about 0.5 M, benzyl alcohol at a concentration of about 2% (v/v), and arginine (e.g., arginine-HCl) at a concentration of about 0.5 M, has a pH of about 6.0.

In some embodiments, a wash solution of the present disclosure comprises benzyl alcohol and/or arginine (e.g., arginine-HCl), and has a pH of about 5.0. In some embodiments, the wash solution comprises benzyl alcohol at a concentration of about 2% (v/v) and/or arginine (e.g., arginine-HCl) at a concentration of about 0.5 M, and has a pH of about 5.0. In some embodiments, the wash solution comprises benzyl alcohol at a concentration of about 2% (v/v) and arginine (e.g., arginine-HCl) at a concentration of about 0.5 M, and has a pH of about 5.0.

In some embodiments, a wash solution of the present disclosure comprises sodium benzoate, arginine (e.g., arginine-HCl), caprylic acid, and/or sodium chloride, and has a pH of about 9.0. In some embodiments, the wash solution comprises sodium benzoate at a concentration of about 0.5 M, arginine (e.g., arginine-HCl) at a concentration of about 0.5 M, caprylic acid at a concentration of about 50 mM, and/or sodium chloride at a concentration of about 0.5M, having a pH of about 9.0. In some embodiments, the wash solution comprises sodium benzoate at a concentration of about 0.5 M, arginine (e.g., arginine-HCl) at a concentration of about 0.5 M, caprylic acid at a concentration of about 50 mM, and sodium chloride at a concentration of about 0.5M, having a pH of about 9.0.

In some embodiments, a wash solution of the present disclosure comprises sodium benzoate, arginine (e.g., arginine-HCl), caprylic acid, and/or sodium chloride, and has a pH of about 7.0. In some embodiments, the wash solution comprises sodium benzoate at a concentration of about 0.5 M, arginine (e.g., arginine-HCl) at a concentration of about 0.5 M, caprylic acid at a concentration of about 50 mM, and/or sodium chloride at a concentration of about 0.5M, having a pH of about 7.0. In some embodiments, the wash solution comprises sodium benzoate at a concentration of about 0.5 M, arginine (e.g., arginine-HCl) at a concentration of about 0.5 M, caprylic acid at a concentration of about 50 mM, and sodium chloride at a concentration of about 0.5M, having a pH of about 7.0.

In some embodiments, a wash solution of the present disclosure comprises sodium benzoate and/or sodium bicarbonate, and has a pH of about 10.0. In some embodiments, the wash solution comprises sodium benzoate at a concentration of about 0.5 M and/or sodium bicarbonate at a concentration of about 50 mM, and has a pH of about 10.0. In some embodiments, the wash solution comprises sodium benzoate at a concentration of about 0.5 M and sodium bicarbonate at a concentration of about 50 mM, and has a pH of about 10.0.

In some embodiments, a wash solution of the present disclosure comprises benzyl alcohol at a concentration of about 4% (v/v), and has a pH of about 5.0 to about 10. In some embodiments, the wash solution comprises benzyl alcohol at a concentration of about 4% (v/v), and has a pH of about 9.0.

Adjusting a Harvest that Comprises a Polypeptide Comprising an Fc Region Prior to Chromatography In one aspect, provided is a method of purifying a polypeptide comprising an Fc region, comprising the steps of: (A) adjusting (A) adjusting a harvest comprising the polypeptide comprising the Fc region to achieve a final concentration of a benzoate salt of about 0.1M and about 0.5M and a pH between about 7.0 and about 9.0 to produce a sample comprising (i) the polypeptide comprising the Fc region, and (ii) one or more impurities; and (B) contacting the sample with at least one chromatography matrix. In some embodiments, the at least one chromatography matrix is an affinity chromatography matrix, e.g., a Protein A chromatography matrix and/or a protein G chromatography matrix. In some embodiments, the method further comprising a step of contacting the at least one chromatography matrix with at least one wash solution. In some embodiments, the method further comprises a step of contacting the at least one chromatography matrix with an elution solution. In some embodiments, the method further comprises the step of collecting an eluate comprising the polypeptide comprising the Fc region.

In some embodiments, the term "harvest" refers to the fluid present at the end of cell culture or after cell culture, e.g., a cell lysate sample, or a cell culture supernatant sample (e.g., a supernatant from cells, such as CHO cells, engineered to produce and secrete the polypeptide). In some embodiments, the harvest comprises intact host cells and/or cellular debris. In some embodiments, the harvest does not comprise intact host cells and/or cellular debris. For example, in some embodiments, the fluid present at the end of cell culture or after cell culture is subject to one or more centrifugation and/or filtration steps prior to adjustment to achieve a final concentration of a benzoate salt of about 0.1M and about 0.5M and a pH between about 7.0 and about 9.0. In some embodiments, the harvest is derived from the fluid present at the end of cell culture or after cell culture. For example, in some embodiments, the fluid present at the end of cell culture or after cell culture is subject to one or more pre-treatment steps to optimize for cell separation and/or purification of the polypeptide comprising an Fc region.

In a related aspect, any one of the methods of purifying a polypeptide comprising an Fc region described herein further comprises a step of adjusting a harvest that comprises a polypeptide comprising an Fc region to achieve a final concentration of a benzoate salt of 0.1 M and about 0.5 M and a pH between about 7.0 and about 9.0 to produce the sample comprising (i) the polypeptide comprising the Fc region, and (ii) one or more impurities.

In some embodiments, the benzoate salt is a benzoate alkali salt. In some embodiments, the benzoate salt is sodium benzoate. In some embodiments, the harvest is adjusted to achieve a final concentration of a benzoate salt (e.g., sodium benzoate) of about any one of 0.025 M, 0.05 M, 0.075 M, 0.1 M, 0.125 M, 0.15 M, 0.175 M, 0.2 M, 0.225 M, 0.25 M, 0.275 M, 0.3 M, 0.325 M, 0.35 M, 0.375 M, 0.4 M 0.425 M, 0.45 M, 0.475 M, 0.5 M, 0.525 M, 0.55 M 0.575 M, 0.6 M, 0.625 M, 0.65 M, 0.675 M, 0.7 M, 0.725 M, 0.75 M. 0.775 M, or 0.8 M, including any range in between these values. In some embodiments, the pH of the harvest is adjusted to about any one of 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0, including any range in between these values. In some embodiments, the harvest is clarified prior to adjustment (e.g., addition of sodium benzoate and adjustment of pH). In some embodiments, the harvest is clarified following adjustment (e.g., addition of sodium benzoate and adjustment of pH).

In some embodiments, the method comprises adjusting the harvest to achieve a final sodium benzoate concentration of about 0.5 M and a pH of about 7. In some embodiments, the method comprises adjusting the harvest to achieve a final sodium benzoate concentration of about 0.1 M and a pH of about 9. In some embodiments, the method comprises adjusting the harvest to achieve a final sodium benzoate concentration of about 0.2 M and a pH of 9. In some embodiments, the method comprises adjusting the harvest to achieve a final sodium benzoate concentration of about 0.3 M and a pH of 9. In some embodiments, the method comprises adjusting the harvest to achieve a final sodium benzoate concentration of about 0.4 M and a pH of 9. In some embodiments, the method comprises adjusting the harvest to achieve a final sodium benzoate concentration of about 0.5 M and a pH of 9.

In some embodiments, adjusting the harvest (e.g., adding sodium benzoate and adjusting of pH) results in the polypeptide comprising the Fc region being purified away from the one or more impurities to a higher degree than a corresponding method lacking the step of adjusting the harvest comprising the polypeptide comprising the Fc region to produce the sample. In some embodiments, one or more impurities are host cell proteins (HCPs), such as phospholipases, clusterin, serine proteases, elongation factors, and any combinations thereof. In some embodiments, the HCP is Putative Phospholipase B-like 2 (PLBL2).

In some embodiments, the adjusted harvest (e.g., to which sodium benzoate has been added to achieve a final concentration described herein and the pH of which has been adjusted as described herein) comprises or is the sample comprising (i) the polypeptide comprising the Fc region, and (ii) one or more impurities. In some embodiments, the sample is contact with at least one chromatography matrix (e.g., the sample is subject to at least one chromatography step). In some embodiments, the at least one chromatography matrix comprises any one or more of: an affinity chromatography matrix, a mixed-mode chromatography matrix (e.g., a multimodal chromatography matrix), a hydrophobic interaction (HIC) chromatography matrix, an anion exchange chromatography matrix, a cation exchange chromatography matrix, a size exclusion chromatography matrix, a ceramic hydroxyapatite (CHT) chromatography matrix, and/or a hydrophilic interaction liquid chromatography (HILIC) matrix, etc., in any order. In some embodiments, the sample is contacted with an affinity chromatography matrix, e.g., a Protein A matrix or a Protein G matrix. In some embodiments, the method further comprising a step of contacting the at least one chromatography matrix with at least one wash solution. In some embodiments, the method further comprises a step of contacting the at least one chromatography matrix with an elution solution. In some embodiments, the method further comprises the step of collecting an eluate comprising the polypeptide comprising the Fc region.

Impurity Removal

Certain aspects of the present disclosure relate to methods of purifying a polypeptide comprising an Fc region via protein A chromatography by washing a protein A matrix bound to the polypeptide comprising an Fc region (e.g., an antibody) with a wash solution comprising a benzoate salt and/or benzyl alcohol, in order to improve purification of the polypeptide away from one or more impurities. In some embodiments, the method comprises the steps of: contacting a protein A chromatography matrix with a sample comprising (1) a polypeptide comprising an Fc region (e.g., an antibody) and (2) one or more impurities (e.g., host cell impurities) under a condition that the polypeptide comprising the Fc region (e.g., the antibody) binds to protein A; and washing the matrix with a wash solution comprising a benzoate salt at a concentration of about 0.1 M to about 1.0 M and/or benzyl alcohol at a concentration of about 0.5% to about 4% volume/volume (v/v), where the wash solution has a pH of about 4.0 to about 10.0. In some embodiments, washing the protein A matrix with the wash solution results in the polypeptide comprising the Fc region being purified away from the one or more impurities to a higher degree than a corresponding method (as described above) lacking the step of washing the matrix with the wash solution.

A standard protein A process typically results in a product purity of about 95% without the use of a wash step as described herein. The largest proportions of the impurities in the product are due to high molecular weight (HMW) aggregates and/or low molecular weight (LMW) fragments of the product. These product variants are considered impurities due to their ability to be separated from the product based on various parameters (e.g., charge, hydrophobicity, size difference, etc.). These HMW and LMW impurities account for about 4-5% of the protein A pool. Furthermore, a standard protein A process lacking the use of a wash step as described herein also typically results in the inclusion of host cell protein (HCP) impurities on the order of 1000 ppm or ~0.1% of the product pool. However, due to the specifications set for injectable mAb products (see e.g., FDA guidelines), reduction and/or complete removal of this 0.1% of HCP impurities is of considerable importance. The inclusion of a step applying a wash solution described herein may reduce the amount of HCPs present in the pool to ~100-10 ppm (a 10 to 100-fold reduction in HCPs relative to the same protein A process lacking the wash step described herein), accounting for a 90-99% relative improvement. Methods of measuring sample protein purity and/or impurity levels (e.g., by ELISA assay) are generally known to one of ordinary skill in the art. An exemplary purification of a monoclonal antibody (mAb) away from one or more host cell proteins using a standard method vs. any of the methods described herein is shown in Table A below.

TABLE A

| exemplary purification process Composition (post protein A) | | | |
|---|---|---|---|
| | HCP | | mAb |
| Condition: | ppm: | % | % |
| Standard | 1000 | 0.10 | 94.90 |
| Including wash step (as described herein) | 100 | 0.01 | 94.99 |
| Change (%) | 90 | 90 | 0.09 |

In some embodiments, the methods described herein produce a protein pool containing a polypeptide comprising an Fc region (e.g., a monoclonal antibody) after protein A elution that contains less than about 500 ppm (parts per million) of HCPs (e.g., one or more HCPs from a CHO cell). For example, a protein pool containing a polypeptide comprising an Fc region produced by the methods described herein may contain less than about 500 ppm, less than about 450 ppm, less than about 400 ppm, less than about 350 ppm, less than about 300 ppm, less than about 250 ppm, less than about 200 ppm, less than about 150 ppm, less than about 100 ppm, less than about 75 ppm, less than about 50 ppm, less than about 25 ppm, less than about 10 ppm, or less than about 1 ppm of HCPs (e.g., one or more HCPs from a CHO cell). In some embodiments, a protein pool containing a polypeptide comprising an Fc region produced by the methods described herein contains less than about 100 ppm of HCPs (e.g., one or more HCPs from a CHO cell). In some embodiments, a protein pool containing a polypeptide comprising an Fc region produced by the methods described herein contains less than about 10 ppm of HCPs (e.g., one or more HCPs from a CHO cell).

In some embodiments, the methods described herein produce a protein pool containing a polypeptide comprising an Fc region (e.g., a monoclonal antibody) after protein A elution that contains less than about 0.1% HCPs (e.g., one or more HCPs from a CHO cell). For example, a protein pool containing a polypeptide comprising an Fc region produced by the methods described herein may contain less than about less than about 0.1%, less than about 0.09%, less than about 0.08%, less than about 0.07%, less than about 0.06%, less than about 0.05%, less than about 0.04%, less than about 0.03%, less than about 0.02%, or less than about 0.01% HCPs (e.g., one or more HCPs from a CHO cell). In some embodiments, a protein pool containing a polypeptide comprising an Fc region produced by the methods described herein contains less than about 0.05% HCPs (e.g., one or more HCPs from a CHO cell). In some embodiments, a protein pool containing a polypeptide comprising an Fc region produced by the methods described herein contains less than about 0.01% HCPs (e.g., one or more HCPs from a CHO cell).

In some embodiments, the methods described herein reduce the amount and/or concentration (e.g., parts per million) of one or more impurities (e.g., one or more HCPs such as one or more HCPs from a CHO cell) co-purified with the polypeptide comprising the Fc region by at least about 10% relative to the amount of the one or more impurities co-purified with a polypeptide comprising an Fc region purified by a corresponding method lacking the step of washing the protein A matrix with the wash solution. For example, the methods described herein reduce the amount and/or concentration (e.g., parts per million) of one or more impurities (e.g., one or more HCPs such as one or more HCPs from a CHO cell) co-purified with the polypeptide comprising the Fc region by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95% or at least about 99% relative to the amount of one or more impurities co-purified with a polypeptide comprising an Fc region purified by a corresponding method lacking the step of washing the protein A matrix with the wash solution. In some embodiments, the methods described herein reduce the amount and/or concentration (e.g., parts per million) of one or more impurities (e.g., one or more HCPs such as one or more HCPs from a CHO cell) co-purified with the polypeptide comprising the Fc region by at least about 1.5-fold relative to the amount of one or more impurities co-purified with a polypeptide comprising an Fc region purified by a corresponding method lacking the step of washing the protein A matrix with the wash solution. For example, the methods described herein reduce the amount and/or concentration (e.g., parts per million) of one or more impurities (e.g., one or more HCPs such as one or more HCPs from a CHO cell) co-purified with the polypeptide comprising the Fc region by at least about 1.5-fold, at least about 2-fold, at least about 2.5-fold, at least about 3-fold, at least about 3.5-fold, at least about 4-fold, at least about 4.5-fold, at least about 5-fold, at least about 5.5-fold, at least about 6-fold, at least about 6.5-fold, at least about 7-fold, at least about 7.5-fold, at least about 8-fold, at least about 8.5-fold, at least about 9-fold, at least about 9.5-fold, at least about 10-fold, at least about 50-fold, or at least about 100-fold relative to the amount of one or more impurities co-purified with a polypeptide comprising an Fc region purified by a corresponding method lacking the step of washing the protein A matrix with the wash solution.

Additional Steps

In some embodiments, the methods described herein further comprise one or more additional wash steps. In some embodiments, the methods described herein further comprise one or more elution steps. In some embodiments, the methods described herein further comprise one or more wash steps and one or more elution steps.

In some embodiments, the present disclosure relates to washing the protein A matrix with a first solution prior to washing the matrix with the wash solution. In some embodiments, the matrix is washed with the first solution one or more (e.g., one or more, two or more, three or more, four or more, five or more, etc.) times prior to washing the matrix with the wash solution. In some embodiments, the matrix is washed once with the first solution prior to washing the matrix with the wash solution. In some embodiments, the first solution comprises a buffer. Any suitable buffer known in the art may be used in the first solution, including, for example, phosphate, tris (tris(hydroxymethyl)methylamine), acetate, carbonate, citrate, bis-tris, bis-tris propane, arginine, histidine, triethanolamine, diethanolamine, formate, IVIES (2-(N-mopholino)ethanesulfonic acid), HEPES (4-2-hydroxyethyl-1-piperazineethanesulfonic acid), MOPS (3-(N-morpholino) propanesulfonic acid), TAPS (3-{[tris (hydroxymehtyl)methyl]amino}propanesulfonic acid), Bicine (N,N-bis(2-hydroxyethyl)glycine), Tricine (N-tris (hydroxymethyl)methylglycine), TES (2-{[tris(hydroxymethyl)methyl]amino}ethanesulfonic acid), PIPES (piperazine-N,N'-bis(2-ethanesulfonic acid), cacodylae (dimethylarsinic acid), SSC (saline sodium citrate), and/or any combinations thereof. In some embodiments, the first solution comprises phosphate buffer, tris buffer, acetate buffer, carbonate buffer, and/or citrate buffer. In some embodiments, the first solution comprises phosphate buffer. In some embodiments, the first solution comprises one or more additional components (e.g., benzoate salt, benzyl alcohol, one or more additives described herein, etc.). In some embodiments, the first solution has a pH of about 5.0 to about 10.0 (e.g., about 6.0 to about 10.0, about 6.0 to about 9.0, about 7.0 to about 10.0, about 7.0 to about 9.0, about 8.0 to about 10.0, about 8.0 to about 9.0, about 9.0 to about 10.0, about 5.0 to about 8.0, about 6.0 to about 8.0, about 7.0 to about 8.0, about 5.0 to about 7.0, about 6.0 to about 7.0, or about 5.0 to about 6.0). In some embodiments, the first solution has a pH of about 7.0.

In some embodiments, the first solution comprises the buffer at a concentration of about 10 mM to about 100 mM or about 10 mM to about 500 mM. For example, the first solution may comprise the buffer at a concentration of about 10 mM to about 500 mM, about 100 mM to about 500 mM, about 150 mM to about 500 mM, about 200 mM to about 500 mM, about 250 mM to about 500 mM, about 300 mM to about 500 mM, about 350 mM to about 500 mM, about 400 mM to about 500 mM, about 450 mM to about 500 mM, about 10 mM to about 450 mM, about 10 mM to about 400 mM, about 10 mM to about 350 mM, about 10 mM to about 300 mM, about 10 mM to about 250 mM, about 10 mM to about 200 mM, about 10 mM to about 150 mM, about 10 mM to about 100 mM, about 25 mM to about 100 mM, about 40 mM to about 100 mM, about 50 mM to about 100 mM, about 60 mM to about 100 mM, about 75 mM to about 100 mM, about 10 mM to about 75 mM, about 25 mM to about 75 mM, about 40 mM to about 75 mM, about 50 mM to about 75 mM, about 60 mM to about 75 mM, about 10 mM to about 60 mM, about 25 mM to about 60 mM, about 40 mM to about 60 mM, about 50 mM to about 60 mM, about 10 mM to about 50 mM, about 25 mM to about 50 mM, about 40 mM to about 50 mM, about 10 mM to about 40 mM, about 25 mM to about 40 mM, or about 10 mM to about 25 mM. In some embodiments, the first solution comprises the buffer at a concentration of about 10 mM to about 50 mM or about 10 mM to about 500 mM.

In some embodiments, the first solution comprises the buffer at a concentration of any of about 10 mM, 15 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM, or 100 mM. Alternatively, the first solution comprises the buffer at a concentration of any of about 150 mM, 200 mM, 250 mM, 300 mM, 350 mM, 400 mM, 450 mM, or 500 mM. In some embodiments, the first solution comprises the buffer at a concentration of about 500 mM. In some embodiments, the first solution comprises the buffer at a concentration of about 50 mM. In some embodiments, the first solution comprises phosphate buffer at a concentration of about 500 mM. In some embodiments, the first solution comprises phosphate buffer at a concentration of about 50 mM.

In some embodiments, the first solution comprises phosphate buffer (e.g., sodium phosphate) and sodium chloride. In some embodiments, the first solution comprises phosphate buffer (e.g., sodium phosphate) and sodium chloride, and has a pH of about 7.0. In some embodiments, the first solution comprises phosphate buffer (e.g., sodium phosphate) at a concentration of about 50 mM, and sodium chloride at a concentration of about 0.5 M. In some embodiments, the first solution comprises phosphate buffer (e.g., sodium phosphate) at a concentration of about 50 mM, and sodium chloride at a concentration of about 0.5 M, and had a pH of about 7.0.

In some embodiments, the present disclosure relates to washing the protein A matrix with a second solution after washing the matrix with the wash solution. In some embodiments, the matrix is washed with the second solution one or more (e.g., one or more, two or more, three or more, four or more, five or more, etc.) times after washing the matrix with the wash solution. In some embodiments, the matrix is washed once with the second solution after washing the matrix with the wash solution. In some embodiments, the second solution comprises a buffer. Any suitable buffer known in the art may be used in the second solution, including, for example, phosphate, tris (tris(hydroxymethyl) methylamine), acetate, carbonate, citrate, bis-tris, bis-tris propane, arginine, histidine, triethanolamine, diethanolamine, formate, IVIES (2-(N-mopholino)ethanesulfonic acid), HEPES (4-2-hydroxyethyl-1-piperazineethanesulfonic acid), MOPS (3-(N-morpholino) propanesulfonic acid), TAPS (3-{[tris(hydroxymehtyl)methyl] amino}propanesulfonic acid), Bicine (N,N-bis(2-hydroxyethyl)glycine), Tricine (N-tris(hydroxymethyl)methylglycine), TES (2-{[tris(hydroxymethyl)methyl] amino}ethanesulfonic acid), PIPES (piperazine-N,N'-bis(2-ethanesulfonic acid), cacodylae (dimethylarsinic acid), SSC (saline sodium citrate), and/or any combinations thereof. In some embodiments, the second solution comprises phosphate buffer, tris buffer, acetate buffer, carbonate buffer, and/or citrate buffer. In some embodiments, the second solution comprises phosphate buffer. In some embodiments, the second solution comprises substantially low salt or no salt. In some embodiments, the second solution has a pH of about 4.0 to about 8.0 (e.g., about 5.0 to about 8.0, about 6.0 to about 8.0, about 7.0 to about 8.0, about 4.0 to about 7.0, about 5.0 to about 7.0, about 6.0 to about 7.0, about 4.0 to about 6.0, about 5.0 to about 6.0, or about 4.0 to about 5.0). In some embodiments, the second solution has a pH of about 5.0 to about 7.0. In some embodiments, the second solution has a pH of about 7.0. In some embodiments, the second solution comprises substantially low salt. In some embodiments, the second solution comprises no salt.

In some embodiments, the second solution comprises the buffer at a concentration of about 10 mM to about 100 mM or about 10 mM to about 500 mM. For example, the second solution may comprise the buff at a concentration of about 10 mM to about 500 mM, about 100 mM to about 500 mM, about 150 mM to about 500 mM, about 200 mM to about 500 mM, about 250 mM to about 500 mM, about 300 mM to about 500 mM, about 350 mM to about 500 mM, about 400 mM to about 500 mM, about 450 mM to about 500 mM, about 10 mM to about 450 mM, about 10 mM to about 400 mM, about 10 mM to about 350 mM, about 10 mM to about 300 mM, about 10 mM to about 250 mM, about 10 mM to about 200 mM, about 10 mM to about 150 mM, about 10 mM to about 100 mM, about 25 mM to about 100 mM, about 40 mM to about 100 mM, about 50 mM to about 100 mM, about 60 mM to about 100 mM, about 75 mM to about 100 mM, about 10 mM to about 75 mM, about 25 mM to about 75 mM, about 40 mM to about 75 mM, about 50 mM to about 75 mM, about 60 mM to about 75 mM, about 10 mM to about 60 mM, about 25 mM to about 60 mM, about 40 mM to about 60 mM, about 50 mM to about 60 mM, about 10 mM to about 50 mM, about 25 mM to about 50 mM, about 40 mM to about 50 mM, about 10 mM to about 40 mM, about 25 mM to about 40 mM, or about 10 mM to about 25 mM. In some embodiments, the second solution comprises the buffer at a concentration of about 10 mM to about 50 mM or about 10 mM to about 500 mM.

In some embodiments, the second solution comprises the buffer at a concentration of any of about 10 mM, 15 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM, or 100 mM. Alternatively, the second solution comprises the buffer at a concentration of any of about 150 mM, 200 mM, 250 mM, 300 mM, 350 mM, 400 mM, 450 mM, or 500 mM. In some embodiments, the second solution comprises the buffer at a concentration of about 500 mM. In some embodiments, the second solution comprises the buffer at a concentration of about 50 mM.

In some embodiments, the second solution comprises phosphate buffer (e.g., sodium phosphate). In some embodiments, the second solution comprises phosphate buffer (e.g., sodium phosphate), and has a pH of about 7.0. In some embodiments, the second solution comprises phosphate buffer (e.g., sodium phosphate) at a concentration of about 50 mM. In some embodiments, the second solution comprises phosphate buffer (e.g., sodium phosphate) at a concentration of about 50 mM, and had a pH of about 7.0.

In some embodiments, the methods of the present disclosure relate to washing a protein A matrix with a wash solution, and do not include a step of washing the matrix with a first solution (prior to the wash solution) or a second solution (after the wash solution). In some embodiments, the methods of the present disclosure relate to washing a protein A matrix with a first solution, then washing the matrix with a wash solution, and do not include a step of washing the matrix with a second solution (after the wash solution). In some embodiments, the methods of the present disclosure relate to washing a protein A matrix with a wash solution and then washing the matrix with a second solution, and do not include a step of washing the matrix with a first solution (prior to the wash solution). In some embodiments, the methods of the present disclosure relate to washing a protein A matrix with a first solution, then washing the matrix with a wash solution, and then washing the matrix with a second solution.

In some embodiments, the protein A matrix is contacted with an elution solution one or more (e.g., one or more, two or more, three or more, four or more, five or more, etc.) times after one or more washing steps. In some embodiments, the matrix is contacted with the elution solution one time. Any solution known in the art suitable for eluting a polypeptide bound to a protein A matrix may be used as an elution solution in the methods of the present disclosure (e.g., an elution solution comprising 40 mM sodium acetate having a pH of about 3.1). In some embodiments, the elution solution further comprises one or more additional components (e.g., arginine at any of the concentrations described herein). In some embodiments, an eluate comprising the polypeptide comprising the Fc region is collected after contacting the matrix with the elution solution. In some embodiments, two or more eluates comprising the polypeptide comprising the Fc region are collected after contacting the matrix two or more times with the elution solution. In some embodiments, the two or more eluates are combined after elution. In some embodiments, the eluate(s) are filtered. Any suitable method of filtering an eluate known in the art may be used including, for example, via depth filtration. In some embodiments, the eluate(s) are filtered via depth filtration.

In some embodiments, eluates from a protein A matrix as described herein may be further processed and/or purified (e.g., using an additional chromatography and/or filtration step (such as by use of one or more of ion exchange chromatography, mixed-mode chromatography, affinity chromatography, hydrophobic interaction chromatography, immobilized metal affinity chromatography, size exclusion chromatography, diafiltration, ultrafiltration, and/or viral removal filtration)), and/or formulated (e.g., preparing a pharmaceutical formulation suitable for administration to a subject in need thereof (such as a human subject)).

The foregoing written description is considered to be sufficient to enable one skilled in the art to practice the present disclosure. The following Examples are offered for illustrative purposes only, and are not intended to limit the scope of the present disclosure in any way. Indeed, various modifications of the present disclosure in addition to those shown and described herein will become apparent to those skilled in the art from the foregoing description and fall within the scope of the appended claims.

EXAMPLES

Example 1: Wash Solutions for Improving or Enhancing Removal of Impurities During Antibody Purification The following example describes the use of various combinations of sodium benzoate and benzyl alcohol in intermediate wash solutions to improve/enhance removal of impurities during protein A chromatography.

Materials and Methods
Sample Preparation

Two separate human monoclonal antibody harvest materials were prepared for protein A chromatography as follows: harvest was generated in a suspension culture of recombinant Chinese Hamster Ovary (CHO) cells engineered to constitutively express either one of the antibodies. The recombinant product was secreted into the culture medium which was then centrifuged and clarified by depth filtration for downstream processing. Clarified harvest material was filtered with a 0.22 µm polyethersulfone (PES) filter prior to loading on the protein A column.

Protein A Chromatography

Protein A resin/columns were prepared as follows: MabSelect Sure LX protein A chromatography resin (GE Healthcare Life Sciences; cat. No. 17-5474) was exchanged via gravity settling with 0.5 M sodium chloride solution. Columns were packed using an AKTA Pure or AKTA Avant (GE Healthcare Life Sciences) using either (A) a 1.0 cm diameter column (Essential Life Solutions 10/250 Snap Column; cat. no. S10/250-PPSL-OE-FP10) or (B) a 0.66 cm diameter column (Omnifit™ 6.6/100; cat. no. 006BCC0610FF). The resin was packed to a bed height of 20 cm±10% for column (A), or to a bead height of 5 cm±10% for column (B). Column qualification was performed using a 1% column volume injection of 1.0 M sodium chloride solution onto the column equilibrated in 0.1 M sodium chloride solution, and the conductivity trace was analyzed using Unicorn Evaluation software. The efficiency of the column needed to be at least 775 theoretical plates per meter, and needed to demonstrate an asymmetry of 0.8-1.8.

Prior to loading the harvest material, columns were flushed with reverse osmosis deionization water to remove storage buffer of 20% ethanol. Subsequently, the column was flushed with 0.5 M acetic acid to ensure removal of any bound entities prior to equilibration. The column was equilibrated with 50 mM phosphate buffer with 0.5 M sodium chloride until the pH of the column was >6.5.

Prepared samples were then loaded onto the protein A columns. Columns were loaded to a target of 40 g/L resin with either mAb A (IgG1 subtype or mAb B (IgG4 subtype). The loaded columns were washed as described above with a phosphate buffer solution containing 50 mM phosphate and 0.5 M sodium chloride. Next, the columns were washed with the test wash solution, followed by a salt free wash with a buffered solution at pH 7. Finally, the antibody was eluted from the column using a solution containing 40 mM sodium acetate at a pH of 3.1. Table 1 below provides an exemplary chromatography process.

TABLE 1 column chromatography process description

| Step | Buffer/Solution | Flow Direction | Residence Time (min) | Volume (CV) |
|---|---|---|---|---|
| Flush | Water for Injection (WFI) | Downflow | 8 | 2.5 |
| Strip | 0.5M acetic acid | Downflow | 5 | 2 |
| Equilibration | 50 mM sodium phosphate, 0.5M sodium chloride, pH 7.0 | Downflow | 5 | 3 |
| Load | mAb harvest, 0.22 µm filtered | Downflow | 5 | |
| Wash 1 | 50 mM sodium phosphate, 0.5M sodium chloride, pH 7.0 | Downflow | 5 | 3 |
| Wash 2 | Test solution | Downflow | 5 | 2 |
| Wash 3 | 50 mM sodium phosphate, pH 7.0 | Downflow | 5 | 3 |
| Elution | 40 mM sodium acetate, pH 3.1 | Downflow | 5 | 2 |
| Strip | 0.5M acetic acid | Downflow | 5 | 3 |
| Post-equilibration | 50 mM sodium phosphate, 0.5M sodium chloride, pH 7.0 | Upflow | 5 | 3 |
| Sanitization | 0.5M sodium hydroxide | Upflow | 5 | 3 |
| Post-equilibration | 50 mM sodium phosphate, 0.5M sodium chloride, pH 7.0 | Upflow | 5 | 2 |
| Storage | 20% ethanol | Upflow | 8 | 2 |

Host Cell Protein Detection

After elution, the antibody samples were tested for the presence of host cell protein (HCP) impurities using the $3^{rd}$ Generation CHO HCP ELISA Kit (Cygnus Technologies) according to the manufacturer's protocol. The HCP ELISA was performed at dilutions between 1:400 and 1:800, and absorbance was read at 450/600 nm using a Spectramax Plus 384 plate reader.

Specific "HCP A" Detection

The concentration of a specific HCP (HCP-A) was quantified in the eluted antibody samples using a commercially available Hamster (CHO) ELISA kit (ICL Labs) according to the manufacturer's protocol. The HCP-A ELISA was performed at dilutions between 1:100 and 1:800, and absorbance was read at 450 nm using a Spectramax Plus 384 plate reader.

Results

Host cell proteins (HCPs) have been shown to co-elute with monoclonal antibodies (mAbs), which may be problematic for downstream applications of these antibodies. To identify potential wash additives capable of reducing the amount of contaminant HCPs that co-elute with a mAb of interest, a 1.7 mL protein A chromatography column was loaded with a sample containing a secreted IgG1 human monoclonal antibody (mAb A) harvested from CHO cells that had been both centrifuged and clarified by depth filtration prior to downstream processing (See Table 1). The columns were first washed with a phosphate buffer solution. Next, the columns were washed with one of a number of test wash solutions containing 50 mM phosphate and an additive, either individually or as a combination with sodium benzoate, benzyl alcohol, and arginine, at pH 7.0 (FIG. 1). Control runs did not incorporate any additive wash. After the test washes, the columns were washed with salt free 50 mM phosphate, pH 7.0. Finally, the monoclonal antibody was eluted from the column and pH adjusted to a pH of 6.0 using 2 M tris base. After adjustment, the eluate pools were filtered using a 0.22 μm PES filter, and were tested for the presence of HCP impurities (FIG. 1). Interestingly, washes containing 2% benzyl alcohol and/or 0.5 M sodium benzoate effectively reduced the levels of contaminating HCPs in the eluted antibody samples. The inclusion of arginine in the wash was also observed to improve HCP clearance.

Next, the specific presence of HCP-A was examined in antibodies eluted from the protein A columns. The test and control wash solutions used in this experiment are indicated in Table 2 below.

TABLE 2

Test wash solutions

| Test solution: | Components: | pH: |
|---|---|---|
| Control | No additional wash | 7.0 |
| 1 | 2% benzyl alcohol; 0.5M sodium benzoate | 7.0 |
| 2 | 2% benzyl alcohol; 0.5M sodium benzoate; 0.5M arginine | 6.0 |
| 3 | 0.5M benzenesulfonate; 0.5M sodium benzoate; 2% benzyl alcohol | 7.0 |
| 4 | 50 mM caprylic acid; 0.5M sodium benzoate; 0.5M arginine, 0.5M sodium chloride | 9.0 |
| 5 | 10% hexylene glycol; 2% benzyl alcohol; 0.5M sodium benzoate | 7.0 |
| 6 | 2% benzyl alcohol; 0.5M sodium benzoate; 0.5M arginine | 6.0 |
| 7 | 2% benzyl alcohol; 0.5M arginine | 5.0 |
| 8 | 0.5M sodium benzoate, 50 mM sodium bicarbonate | 10.0 |
| 9 | 2% benzyl alcohol, 0.5M sodium benzoate, 0.5M arginine, 40 mM sodium phosphate | 9.0 |

Figure 2A:
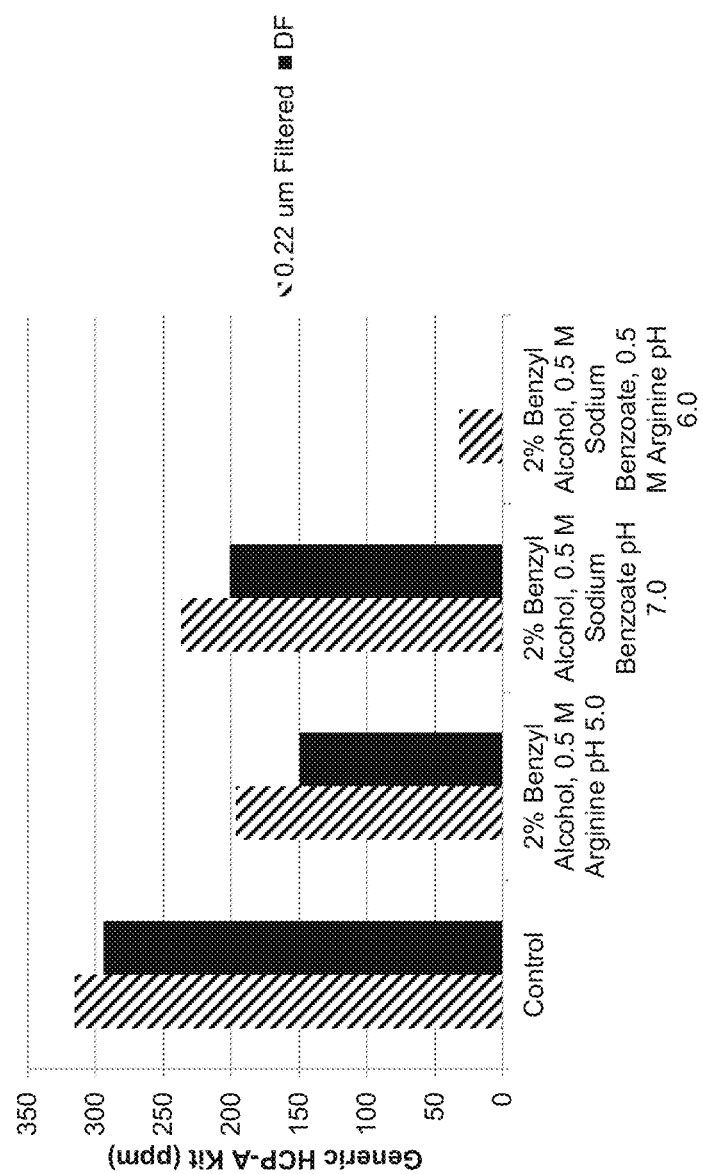
FIGS. 2A-B show the concentrations of a specific HCP (HCP-A) in antibody samples eluted from protein A columns.

Having demonstrated the ability of the combination of benzyl alcohol and sodium benzoate to remove HCP impurities, additional formulations were tested to target removal of HCP-A. An IgG4 antibody (mAb B) with known high HCP-A expression was used to specifically increase HCP-A burden on the column. Table 1 provides a summary of the steps performed during the purification process. Briefly, after equilibration to load pH and conductivity, a 15.7 mL protein A chromatography column was loaded with a sample containing the secreted human monoclonal antibody harvested from CHO cells via both centrifugation and clarification by depth filtration prior to downstream processing. Once a 40 g/L (of resin) load was reached, the column was re-equilibrated using the phosphate buffer solution. One of the washes (test solutions 1, 2, and 7) depicted in Table 2 was then applied as 2 column volumes (CVs), and immediately followed by 3 CVs of salt-free phosphate buffer solution at pH 7.0. After elution with 40 mM sodium acetate, the eluate pools were adjusted to pH 5.5 using 2 M Tris base. Eluate pools were then filtered with either a 0.22 μm PES filter or a Millipore COHC Depth Filter, and were tested for HCP-A content by ELISA (FIG. 2A). All three wash conditions (test solutions 1, 2, and 7) were capable of clearing additional HCP-A relative to the control (294 ppm). The results also suggested that the effect of removal of HCP-A was cumulative, as combination of benzyl alcohol, sodium benzoate, and arginine removed almost 90% of the HCP-A relative to the control. Furthermore, depth filtration provided a subsequent 15-25% additional HCP-A removal for wash condition eluates.

Figure 2B:
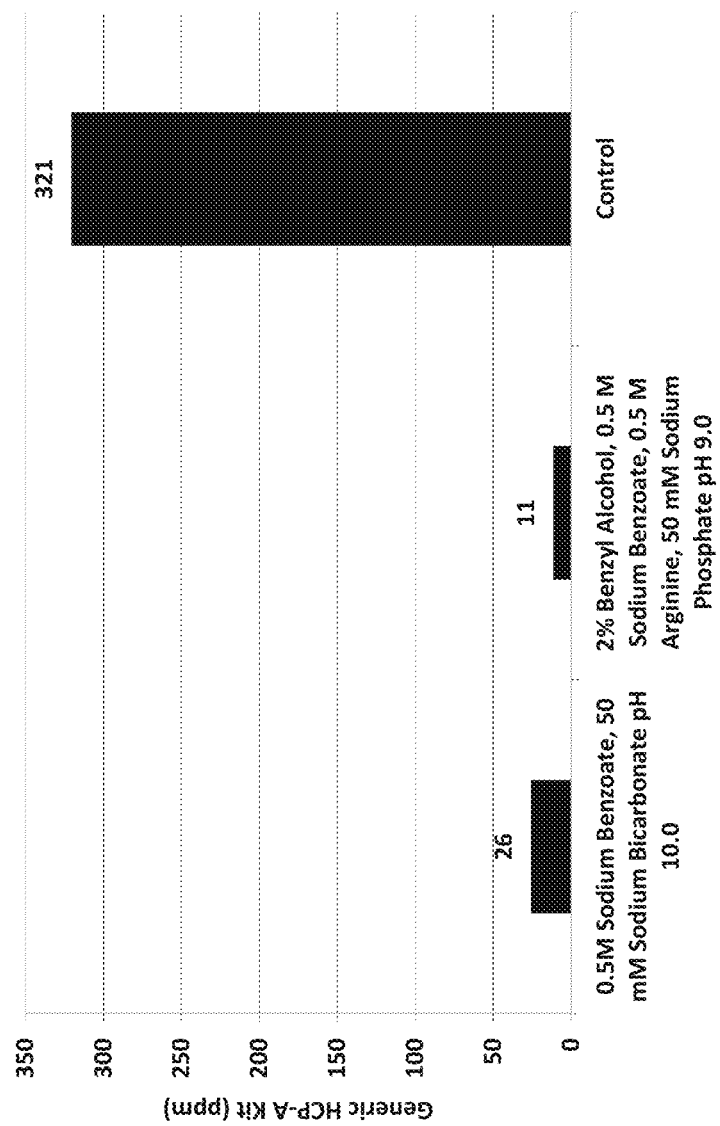

Following a similar procedure as described above, the effectiveness of high pH washes was next tested by washing the columns at a pH of 9.0 or 10.0. An IgG4 antibody (mAb B) was produced in a cell line with known high HCP-A expression to specifically increase HCP-A burden on the protein A column. Table 1 provides a summary of the steps performed during the purification process. Briefly, after equilibration to load pH and conductivity, a 15.7 mL protein A chromatography column was loaded with a sample containing the secreted human monoclonal antibody harvested from CHO cells harvested via both centrifugation and clarification by depth filtration prior to downstream processing. Once a 60 g/L (of resin) load was reached, the column was re-equilibrated using a phosphate buffer solution. One of either test solution 8 or 9 (Table 2) was when applied for two CVs, and immediately followed by three CVs of salt-free phosphate buffer solution at pH 7.0. After elution with 40 mM sodium acetate, the eluate pools were adjusted to pH 5.5 using 2 M tris base. Eluate pools were then filtered with a 0.22 μm PES filter. As shown in FIG. 2B, 0.5 M sodium benzoate with a buffering salt at pH 10.0 was highly effective at removing HCP-A (92% reduction) relative to the control. Furthermore, the addition of benzyl alcohol and arginine were again complementary and increased clearance of HCP-A at pH 9.0. Taken together, the results depicted in FIGS. 2A-B show that robust range of pH which allowed for significant clearance of HCP-A.

Figure 3:
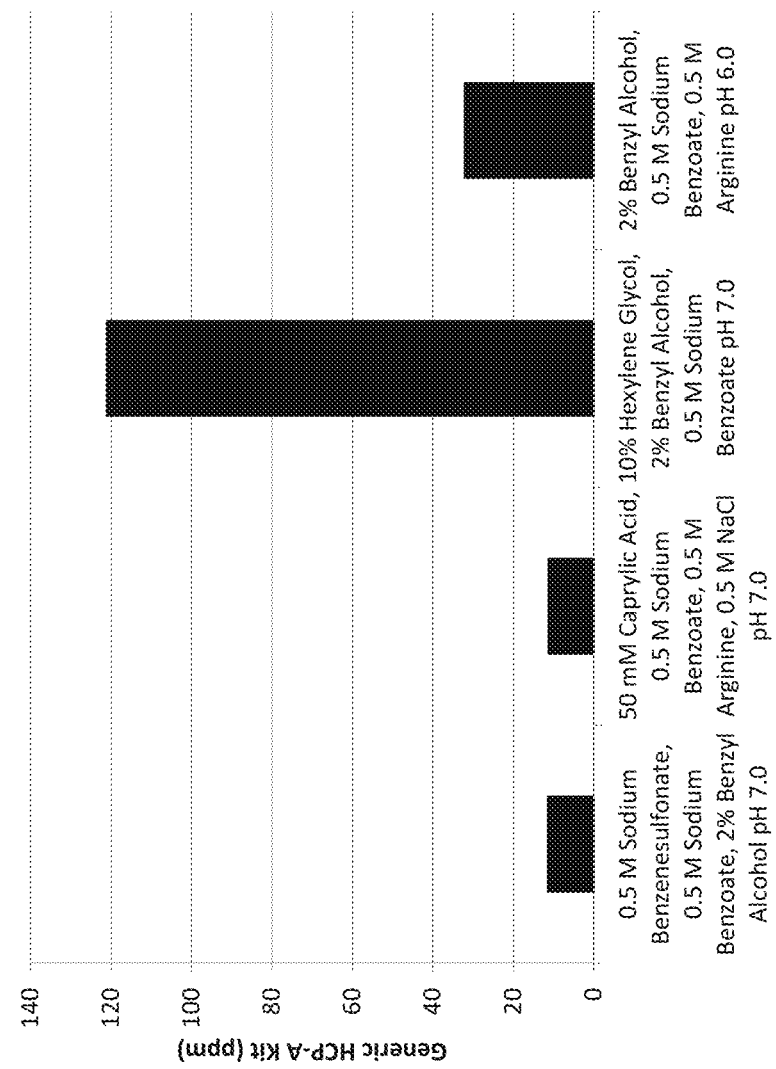
FIG. 3 shows the concentration of HCP-A in antibody samples eluted from protein A columns after being washed with the indicated wash solutions containing additional test compounds, as assessed by ELISA.

Finally, additional additives were screened to further enhance a wash of 2% benzyl alcohol and 0.5 M sodium benzoate. The same IgG4 mAb (mAb B) was used on a 1.7 mL scale column. Table 1 provides a summary of the steps performed during the purification process. Briefly, the column was loaded to 40 g/L following equilibration. One of four of the washes (test solutions 3-6) depicted in Table 2 was then applied to the column. After, elution samples were adjusted to pH 5.5 with 2 M Tris base, and were filtered using a 0.22 μm PES filter. HCP-A content was then measured using an HCP-A-specific ELISA (FIG. 3). Washes with the test solutions demonstrated the cumulative response in HCP-A removal due to the addition of arginine, caprylic acid, benzenesulfonate, and hexylene glycol compared to the 2% benzyl alcohol and 0.5 M sodium benzoate combination (201.3 ppm). A wash containing 2% benzyl alcohol, 0.5 M sodium benzoate, and a component selected from hexylene glycol, sodium benzenesulfonate, caprylic acid, or arginine was highly effective at removing HCP-A.

Taken together, the data provided in this example shows that an intermediate wash step containing sodium benzoate and/or benzyl alcohol was able to provide superior clearance of host cell protein impurities during protein A purification of a human monoclonal antibody. Moreover, the inclusion of one or more additives selected from benzenesulfonate, caprylic acid, hexylene glycol, and/or arginine to the wash solution further improved clearance of host cell protein impurities during protein A purification of the target monoclonal antibody.

Example 2: Identification of Specific Host Cell Proteins Present Following Protein a Chromatography, Development of Wash Solutions for Improving or Enhancing Removal of Impurities During Antibody Purification, and Assessment of Putative Phospholipase B-Like 2 Interaction with Human Monoclonal Antibody The following example describes identification of specific host cell proteins (HCPs) in the purified antibody eluate following protein A chromatography. The example further describes use of sodium benzoate and benzyl alcohol in intermediate wash solutions to improve/enhance removal of HCPs including Putative Phospholipase B-like 2 (PLBL2) during protein A chromatography. Finally, the example describes the effect of loading conditions on protein A chromatography efficiency.

Materials and Methods
Sample Preparation

Human monoclonal antibody harvest materials were prepared for protein A chromatography as described in Example 1. Briefly, harvest was generated in a suspension culture of recombinant CHO cells engineered to constitutively express either one of the human monoclonal antibodies. The recombinant product was secreted into the culture medium which was then centrifuged and clarified by depth filtration for downstream processing. Clarified harvest material was filtered with a 0.22 µm polyethersulfone (PES) filter prior to loading on the protein A column.

Protein A Chromatography

Protein A resin/columns were prepared as described in Example 1. Briefly, Mab Select Sure LX Protein A chromatography resin (GE Healthcare Life Sciences; cat. No. 17-5474) was exchanged via gravity settling with 0.5 M sodium chloride solution. Columns were packed using an AKTA Pure or AKTA Avant (GE Healthcare Life Sciences) using either (A) a 1.0 cm diameter column (Essential Life Solutions 10/250 Snap Column; cat. no. S10/250-PPSL-OE-FP10) or (B) a 0.66 cm diameter column (Omnifit™ 6.6/100; cat. no. 006BCC0610FF). The resin was packed to a bed height of 20 cm±10% for column (A), or to a bead height of 5 cm±10% for column (B). Column qualification was performed using a 1% column volume injection of 1.0 M sodium chloride solution onto the column equilibrated in 0.1 M sodium chloride solution, and the conductivity trace was analyzed using Unicorn Evaluation software. The efficiency of the column needed to be at least 775 theoretical plates per meter, and needed to demonstrate an asymmetry of 0.8-1.8.

Prior to loading the harvest material, columns were flushed with reverse osmosis deionization water to remove storage buffer of 20% ethanol. Subsequently, the column was flushed with 0.5 M acetic acid to ensure removal of any bound entities prior to equilibration. The column was equilibrated with 50 mM phosphate buffer with 0.5 M sodium chloride until the pH of the column was >6.5.

Prepared samples were then loaded onto the protein A columns. Generally, columns were loaded to a target of 40 g/L resin with either human monoclonal antibody A (IgG1 subtype or human monoclonal antibody B (IgG4 subtype). The loaded columns were washed as described above with a phosphate buffer solution containing 50 mM phosphate and 0.5 M sodium chloride. Next, the columns were washed with the test wash solution, followed by a salt free wash with a buffered solution at pH 7. However, control treatments were not washed with a test wash solution. Finally, the antibody was eluted from the column using a solution containing 40 mM sodium acetate at a pH of 3.1. Table 1 provides an exemplary chromatography process.

HCP Detection by Mass Spectrometry

Following protein A column purification and elution under standard conditions, human monoclonal antibody eluates were analyzed by Mass Spectrometry to determine the relative amount of each HCPs. Specifically, the relative amount of Clusterin and Putative Phospholipase B-like 2 (PLBL2) were identified in the protein A purified human monoclonal antibody samples. Mass spectroscopy was performed using an Acquity H-Class Xevo G2-XS Q-Tof and a 2.1×150 mm ACQUITY UPLC column 1.7 µm CSH C18. Samples were first denatured using 0.05% Rapigest in 50 mM Ammonium Bicarbonate and then reduced and alkylated using 20 mM DTT (dithiothreitol) and 40 mM IAA (Iodoacetamide). Enzymatic digestion was performed by 2% LysC overnight followed by 3 hours with 4% Trypsin. Rapigest was removed via centrifugation and samples were acidified using formic acid. A spike-in internal standard of 2.5 fmol/ul of ClpB *E. coli* was then added to compare relative amounts of HCP and PLBL2. A lock mass calibration was performed around 785.8426 m/z. $MS^E$ was used to analyze the ion data and identify HCPs.

HCP Detection by ELISA

Following elution, the presence of generic HCPs in human monoclonal antibody samples was assessed as described in Example 1. Briefly, the antibody samples were tested for the presence of HCP impurities using the $3^{rd}$ Generation CHO HCP ELISA Kit (Cygnus Technologies) according to the manufacturer's protocol. The HCP ELISA was performed at dilutions between 1:400 and 1:800, and absorbance was read at 450/600 nm using a Spectramax Plus 384 plate reader.

PLBL2 Detection by ELISA

The concentration of a PLBL2 was quantified in the eluted antibody samples using a commercially available Hamster (CHO) ELISA kit (ICL Labs, E-65PLB) in accordance with the manufacturer's protocol. The PLBL2 ELISA was performed at dilutions between 1:100 and 1:800, and absorbance was read at 450 nm using a Spectramax Plus 384 plate reader.

Results
Detection of HCPs by Mass Spectrometry

Following protein A purification, HCPs have been shown to co-elute with human monoclonal antibody, which may be problematic for downstream applications of these antibodies. To identify specific HCPs present in the purified human monoclonal antibody solution following protein A purification, a 1.7 mL protein A chromatography column was loaded with a sample containing a secreted IgG1 human monoclonal antibody (mAb A) harvested from CHO cells that had been both centrifuged and clarified by depth filtration prior to downstream processing (See Table 1). The columns were first washed with a phosphate buffer solution. Next, the columns were washed with salt free 50 mM phosphate, pH 7.0. Finally, the monoclonal antibody was eluted from the column and pH adjusted to a pH of 6.0 using 2 M tris base. After adjustment, the eluate pools were filtered using a 0.22 µm PES filter, and were analyzed by Mass Spectrometry to identify relative amounts of HCPs. Notably, Clusterin and PLBL2 were the two most abundant HCPs present in the human monoclonal antibody eluate.

Identification of Intermediate Wash Conditions to Improve HCP/PLBL2 Removal.

Figure 4A:
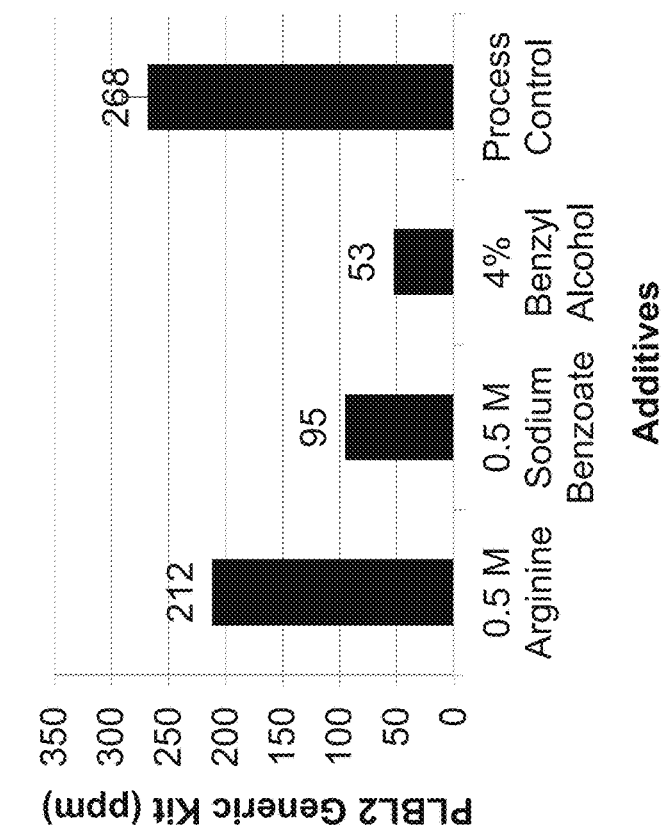
FIGS. 4A-B show the concentrations of generic HCP and PLBL2 in antibody samples eluted from protein A columns.
Figure 4B:
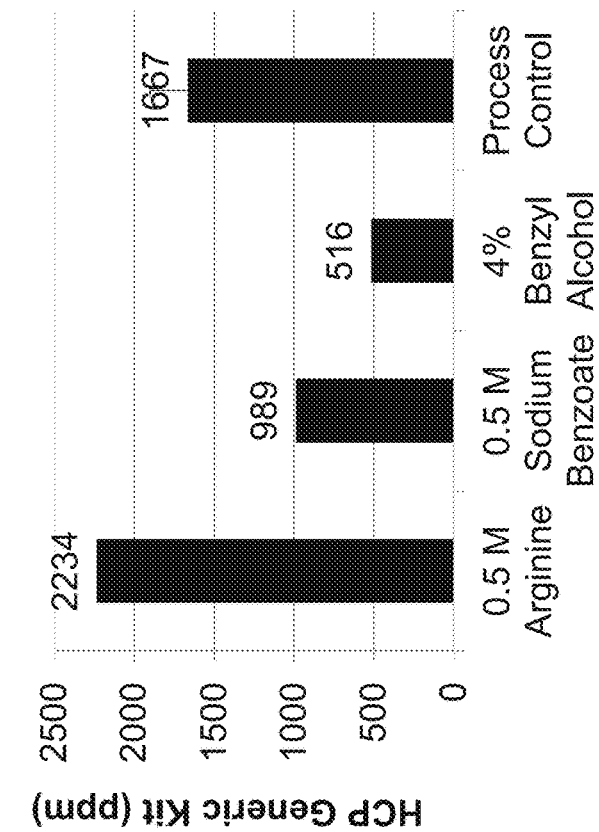

The Mass Spectrometry analysis detailed above provided further evidence that HCPs, including PLBL2, co-elute with human monoclonal antibodies following protein A purification. Next, ELISA screens were developed to identify intermediate wash solutions that could be used to further improve and enhance HCP and PLBL2 removal (FIGS. 4A and 4B). Interestingly, intermediate washes comprising 4% benzyl alcohol or 0.5 M sodium benzoate effectively reduced the levels of contaminating HCPs and PLBL2 in the antibody eluate samples. Washes containing 0.5 M Arginine alone did not reduce level of generic HCPs, but did reduce the level of contaminating PLBL2.

PLBL2 ELISA screens further show that deep filtering combined with intermediate washes comprising: 1) 2% benzyl alcohol and 0.5 M arginine pH 5.0, 2) 2% benzyl alcohol and 0.5 M sodium benzoate pH 7.0, or 3) 2% benzyl alcohol, 0.5 M sodium benzoate, 0.5 M arginine pH 6.0, effectively removed PLBL2 during protein A purification. In addition, washes with elevated pH levels (0.5 M sodium benzoate and 50 mM sodium bicarbonate pH 10.0 or 2% benzyl alcohol, 0.5 M sodium benzoate, 0.5 M arginine, and 50 mM sodium phosphate pH 9.0) were highly effective at removing PLBL2 during protein A purification. Indeed, sodium benzoate wash with 50 mM sodium bicarbonate pH 10.0 was able to remove more than 92% of PLBL2 compared to control treatment. Last, washes comprising: 1) 0.5 M sodium benzoate, 2% benzyl alcohol, and 0.5 M benzenesulfonate pH 7.0, 2) 0.5 M sodium benzoate, 50 mM caprylic acid, 0.5 M arginine, and 0.5 M sodium chloride pH 7.0, 3) 0.5 M sodium benzoate, 2% benzyl alcohol, and 10% hexylene glycol pH 7.0, or 4) 0.5 M sodium benzoate, 2% benzyl alcohol, and 0.5 M arginine pH 6.0, demonstrated robust ability to remove PLBL2 compared to control washes.

Figure 5:
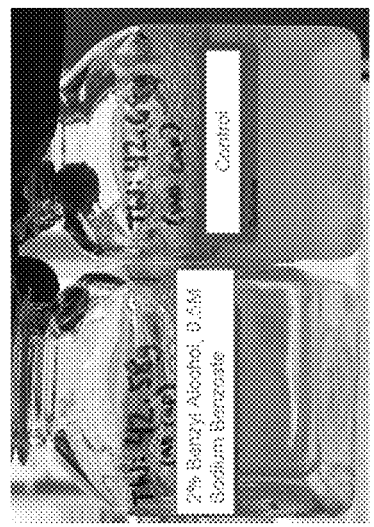
FIG. 5 shows the improvement in visual clarity of antibody samples eluted from protein A columns washed with an intermediate wash comprising 2% Benzyl Alcohol and 0.5 M Sodium Benzoate.

Further, visual comparison of antibody eluate following both experimental and control washes revealed that samples washed with 2% Benzyl Alcohol and 0.5 M Sodium Benzoate had improved clarity relative to control washed samples (FIG. 5).

PLBL2 ELISAs, detailed above, demonstrate that intermediate wash containing benzyl alcohol and sodium benzoate can effectively reduce the level of PLBL2 in protein A purified antibody eluate. Next, this result was further confirmed orthogonally through Mass Spectrometry. The Mass Spectrometry results show that test wash 0.5 M Sodium Benzoate, 0.5 M Arginine, 50 mM Caprylic Acid, 0.5 M NaCl pH 9.0 removed nearly 93% of PLBL2 from the eluate relative to the control treatment.

Assessing the Impact of Column Loading on Yield and PLBL2 Removal

Figure 6A:
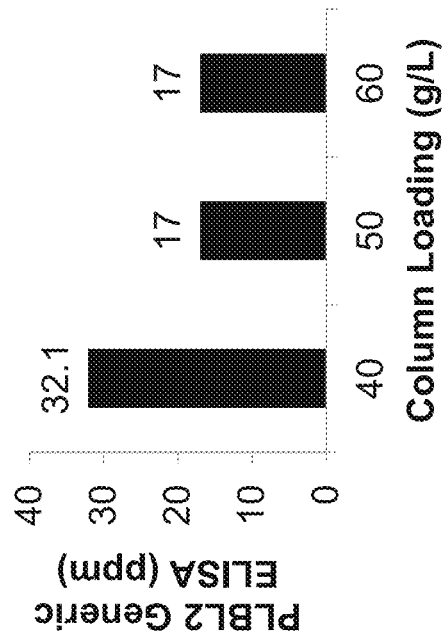
FIGS. 6A-B show the decrease in off-column yield and PLBL2 removal when loading protein A columns beyond 40 g/L.
Figure 6B:
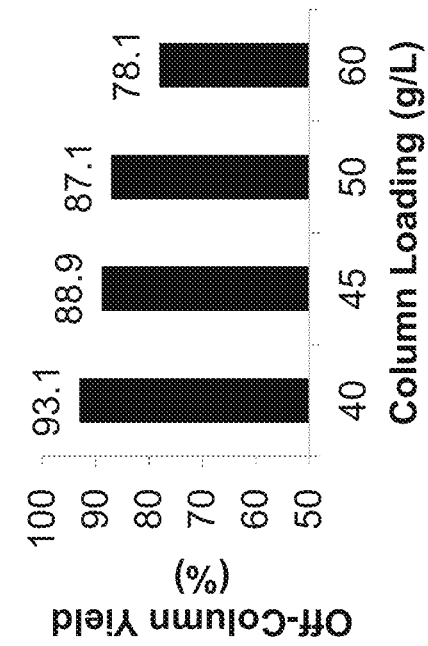

The experiments above demonstrate that host cell protein PLBL2 is present in protein A purified antibody eluate and can be effectively removed using intermediate wash solutions containing Benzyl Alcohol and Sodium Benzoate. Next, the impact of protein A column loading level on off-column yield and PLBL2 removal was assessed. To identify the ideal loading conditions to maximize both off-column yield and PLBL2 removal, protein A columns were loaded at ranges from 40-60 g/L (FIGS. 6A and 6B). The results demonstrate that increasing column load beyond 40 g/L decreases both off-column yield and PLBL2 removal.

Taken together, the data provided in this example show that PLBL2 is among the host cell proteins that co-elute with human monoclonal antibody following protein A purification. Further, the data demonstrate that an intermediate wash step containing sodium benzoate and/or benzyl alcohol was able to provide superior clearance of host cell protein impurities and PLBL2 during protein A purification of a human monoclonal antibody. Moreover, the data show that overloading the protein A resin column can decrease off-column yield and PLBL2 removal.

Example 3: Assessing the Effects of pH and Benzoate Salt Concentration in a Harvest Comprising an Antibody on the Removal of Impurities During Antibody Purification The following example describes experiments that were performed to determine whether adjusting the sodium benzoate concentration and pH of a harvest comprising a monoclonal antibody improves or enhances the removal of impurities during purification of the antibody.

Human monoclonal antibody harvests were prepared as described in Example 1. The clarified and depth filtered harvest was adjusted to varying pH and additive concentrations to screen for impacts on HCP and PLBL2 clearance. Sodium benzoate, previously shown to be effective for PLBL2 removal as part of an additional wash step, was added as a solid in quantities sufficient to reach a target final concentration for a given volume of harvest. After addition, the target pH was reached through addition of 2 M tris base. A first harvest was supplemented with sodium benzoate to achieve a final concentration of 0.5 M sodium benzoate and adjusted to a pH of 7.2. A second harvest was supplemented with sodium benzoate to achieve a final concentration of 0.5 M sodium benzoate and adjusted to a pH of 9. A third harvest was adjusted to a pH of 9 (no sodium benzoate was added). See Table 3:

TABLE 3

| Harvest Additives | pH |
|---|---|
| Tris Base Adjustment Only | 9.0 |
| 0.5M Sodium Benzoate | 7.2 |
| 0.5M Sodium Benzoate | 9.0 |

Once each harvest was adjusted and 0.22 μm filtered, three protein A columns were each loaded to a target of 50 g/L resin with the adjusted harvest. The loaded columns were washed with a phosphate buffer solution containing 50 mM phosphate and 0.5 M sodium chloride. Next, the columns were washed with reverse osmosis de-ionized (RODI) water. Finally, the antibody was eluted from the column using a solution containing 40 mM sodium acetate at a pH of 3.1. Table 4 below provides an exemplary chromatography process.

TABLE 4

| Step | Buffer/Solution | Flow Direction | Residence Time (min) | Volume (CV) |
|---|---|---|---|---|
| Flush | Water for Injection (WFI) | Downflow | 8 | 2.5 |
| Strip | 0.5M acetic acid | Downflow | 5 | 2 |
| Equilibration | 50 mM sodium phosphate, 0.5M sodium chloride, pH 7.0 | Downflow | 5 | 3 |
| Load | Adjusted mAb harvest, 0.22 μm filtered | Downflow | 5 | |
| Wash 1 | 50 mM sodium phosphate, 0.5M sodium chloride, pH 7.0 | Downflow | 5 | 3 |
| Wash 2 | Reverse Osmosis De-Ioninized (RODI) water | Downflow | 5 | 2 |
| Elution | 40 mM sodium acetate, pH 3.1 | Downflow | 5 | 2 |

TABLE 4-continued

| Step | Buffer/Solution | Flow Direction | Residence Time (min) | Volume (CV) |
|---|---|---|---|---|
| Strip | 0.5M acetic acid | Downflow | 5 | 3 |
| Post-equilibration | 50 mM sodium phosphate, 0.5M sodium chloride, pH 7.0 | Upflow | 5 | 3 |
| Sanitization | 0.5M sodium hydroxide | Upflow | 5 | 3 |
| Post-equilibration | 50 mM sodium phosphate, 0.5M sodium chloride, pH 7.0 | Upflow | 5 | 2 |
| Storage | 20% ethanol | Upflow | 8 | 2 |

Figure 7:
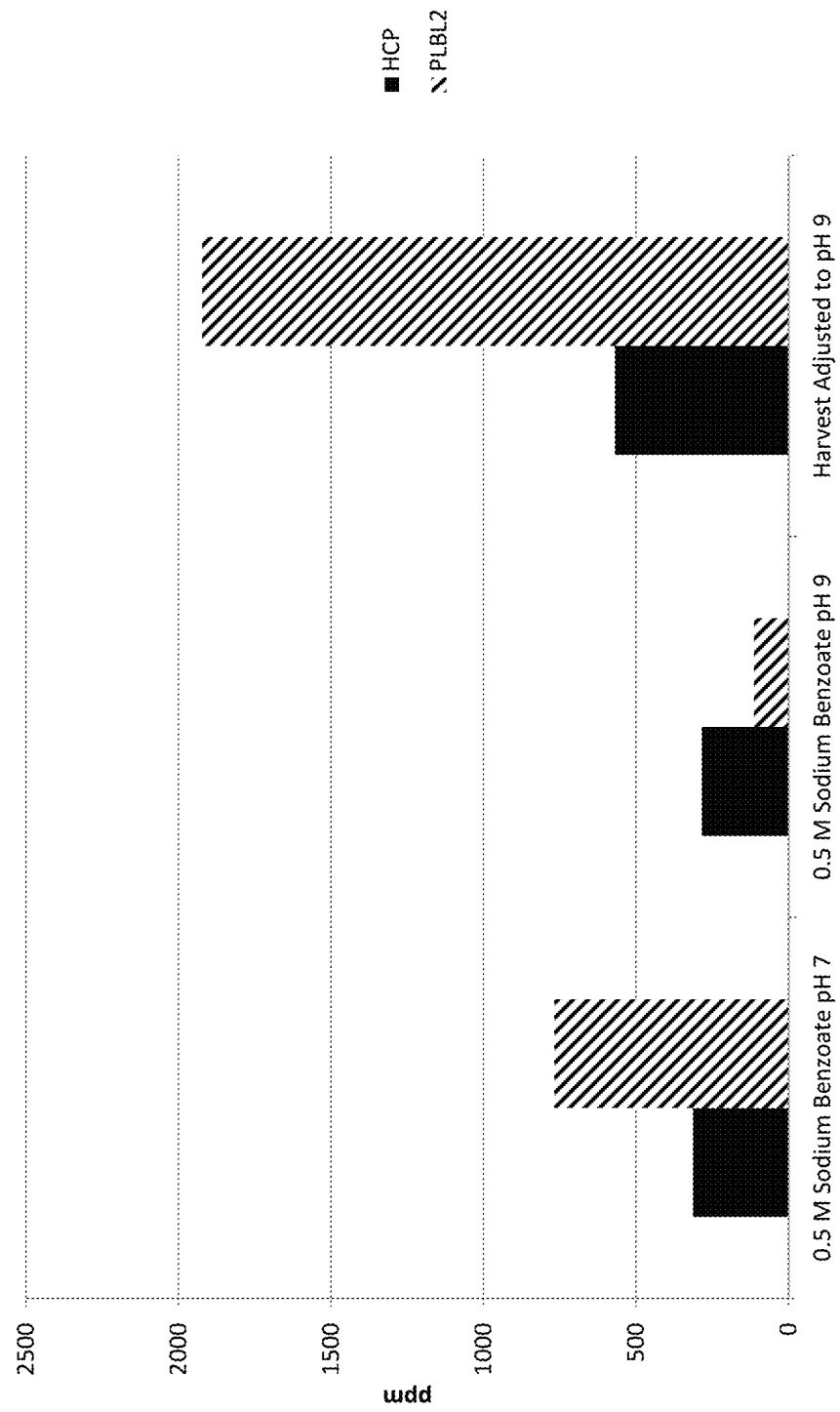
FIG. 7 shows that harvest adjustment to 0.5 M sodium benzoate and pH 7.2 or harvest adjustment to 0.5 M sodium benzoate and pH 9 prior to protein A purification led to improved removal of PLBL2 and HCP impurities. Harvest adjustment to 0.5 M sodium benzoate at pH 9.0 showed the lowest level of PLBL2 and HCP impurities and demonstrated a log greater of PLBL2 clearance relative to a pH adjustment alone.

Each of the three Protein A eluates was then tested for the presence of host cell protein (HCP) impurities via ELISA as described in Example 1, and for the presence of PLBL2 via custom ELISA. As shown in FIG. 7, 0.5 M sodium benzoate at pH 9.0 showed the lowest level of PLBL2 and HCP impurities and demonstrated a log greater of PLBL2 clearance relative to a pH adjustment alone. When 0.5 M sodium benzoate was added to the harvest at pH 7.2, only HCP clearance was improved. Both pH and sodium benzoate adjustment to the harvest were required for an effect on PLBL2. HMW was not impacted by the adjustments (not shown). Compared to unadjusted harvest with only a RODI wash during the Protein A step, HCP was reduced by 65% while PLBL2 was reduced by approximately 79%.

Next, harvests were supplemented with sodium benzoate achieve a final concentration of 0.1 M, 0.2 M, 0.3 M, 0.4 M, or 0.5 M and adjusted to a pH of 9 prior to protein A purification, as described above. See Table 5.

TABLE 5

| Harvest Additives | pH |
|---|---|
| 0.1M Sodium Benzoate | 9.0 |
| 0.2M Sodium Benzoate | 9.0 |
| 0.3M Sodium Benzoate | 9.0 |
| 0.4M Sodium Benzoate | 9.0 |
| 0.5M Sodium Benzoate | 9.0 |

Figure 8:
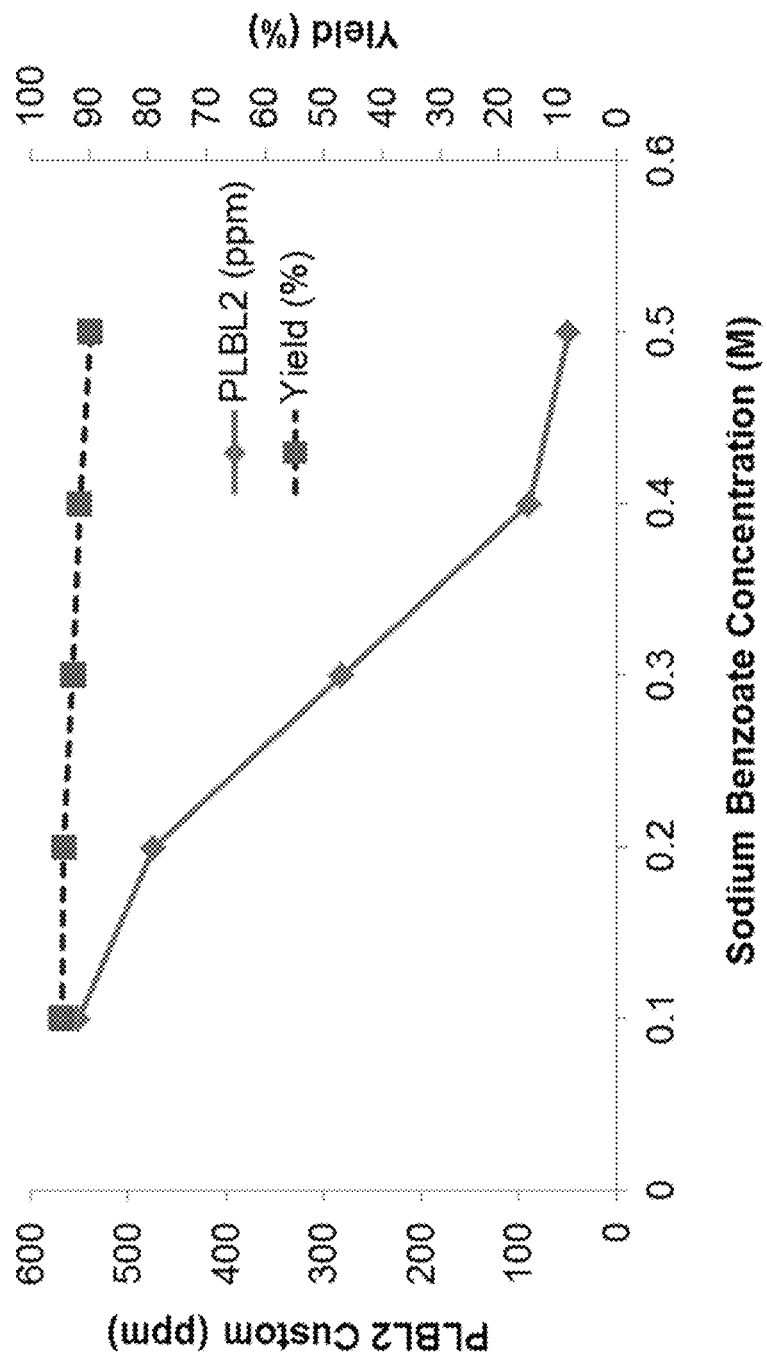
FIG. 8 shows the relationship between PLBL2 content and sodium benzoate concentration is approximately sigmoidal. Diminished gains in clearance of PLBL2 were observed for concentrations above 0.4 M sodium benzoate.

Each Protein A eluate was then tested for the presence of PLBL2 via custom ELISA, and the yield of antibody in each eluate was assessed. FIG. 8 shows the relationship between PLBL2 content and sodium benzoate concentration is approximately sigmoidal. Diminished gains in clearance of PLBL2 were observed for concentrations above 0.4 M sodium benzoate. Antibody yield decreased slightly with increasing concentration of sodium benzoate. From 0.1 M to 0.5 M sodium benzoate, antibody yield decreased from 94.8% to 89.4%. Highest yield and highest PLBL2 clearance were observed when the harvest was adjusted to 0.4 M sodium benzoate and pH 9.0 prior to Protein A purification. Increasing the sodium benzoate concentration above 0.4 M resulted in reduced gains in clearance at the expense of slightly decreased antibody yield. All samples of 0.1 M sodium benzoate had comparable HCP clearance to around 250 ppm. At 0.1 M sodium benzoate and below, the HCP was around 500 ppm. Sodium benzoate concentration between 0.2 M and 0.5 M did not impact the charge variance profile and all eluates were within specified limits.

Taken together, these data suggest that the presence of sodium benzoate in solution renders the association of host cell impurities with the mAb highly unfavorable at high pHs. These conditions can be achieved either through a separate wash step after the mAb has been bound to the protein A resin or in solution prior to or during the load phase of the column. This provides greater flexibility in operation of the protein A purification step and further supports the unique properties of sodium benzoate as a wash additive.

Although the foregoing disclosure has been described in some detail by way of illustration and example for purposes of clarity and understanding, the descriptions and examples should not be construed as limiting the scope of the present disclosure.

What is claimed is:

1. A method of purifying a polypeptide comprising an Fc region, the method comprising the steps of:
   (a) contacting a Protein A chromatography matrix with a sample comprising (i) the polypeptide comprising the Fc region, and (ii) one or more impurities, under a condition that the polypeptide comprising the Fc region binds to Protein A; and
   (b) washing the matrix with a wash solution, wherein the wash solution comprises one or both of (i) a benzoate salt at a concentration of about 0.1 M to about 1.0 M and (ii) benzyl alcohol at a concentration of about 0.5% to about 4% volume/volume (v/v), and wherein the wash solution has a pH of about 4.0 to about 10.0.

2. The method of claim 1, wherein the benzoate salt is a benzoate alkali salt or sodium benzoate.

3. The method of claim 2, wherein the benzoate salt is sodium benzoate, and wherein the sodium benzoate is at a concentration from about 0.1 M to about 0.3 M or 0.5 M.

4. The method of claim 1, wherein the wash solution further comprises a buffering agent selected from the group consisting of phosphate, tris, arginine, acetate, and citrate, and wherein the buffering agent is at a concentration of about 10 mM to about 500 mM.

5. The method of claim 1, wherein the wash solution further comprises one or more of: (a) sodium benzenesulfonate at a concentration of about 0.1 M to about 0.5 M; (b) caprylic acid at a concentration of about 10 mM to about 50 mM; (c) hexylene glycol at a concentration of about 1% to about 10% (v/v); or (d) creatine at a concentration of about 10 mM to about 100 mM.

6. The method of claim 1, wherein the wash solution further comprises arginine at a concentration of about 0.1 M to about 1.0 M, and wherein the wash solution comprising arginine has a pH of about 4.0 to about 6.0 or about 8.0 to 10.0.

7. The method of claim 1, wherein the wash solution further comprises one or more non-buffering salts selected from the group consisting of sodium chloride, sodium bromide, potassium chloride, potassium bromide, magnesium chloride, magnesium bromide, calcium chloride, calcium bromide, and any combinations thereof.

8. The method of claim 1, wherein the wash solution is a solution selected from the group consisting of:
   (i) a solution comprising sodium benzoate at a concentration of about 0.5 M, and sodium bicarbonate at a concentration of about 50 mM, having a pH of about 10.0;
   (ii) a solution comprising sodium benzoate at a concentration of about 0.5 M, benzyl alcohol at a concentration of about 2%, arginine at a concentration of about 0.5 M, and sodium phosphate at a concentration of about 50 mM, having a pH of about 9.0;
   (iii) a solution comprising sodium benzoate at a concentration of about 0.5 M and benzyl alcohol at a concentration of about 2% (v/v), having a pH of about 7.0;
   (iv) a solution comprising sodium benzoate at a concentration of about 0.5 M, benzyl alcohol at a concentration of about 2% (v/v), and sodium chloride at a concentration of about 0.5 M, having a pH of about 7.0;
(v) a solution comprising hexylene glycol at a concentration of about 10% (v/v), sodium benzoate at a concentration of about 0.5 M, and benzyl alcohol at a concentration of about 2% (v/v), having a pH of about 7.0;
(vi) a solution comprising benzenesulfonate at a concentration of about 0.5 M, sodium benzoate at a concentration of about 0.5 M, and benzyl alcohol at a concentration of about 2% (v/v), having a pH of about 7.0;
(vii) a solution comprising caprylic acid at a concentration of about 50 mM, sodium benzoate at a concentration of about 0.5 M, arginine at a concentration of about 0.5 M, and sodium chloride at a concentration of about 0.5 M, having a pH of about 7.0;
(viii) a solution comprising sodium benzoate at a concentration of about 0.5 M, benzyl alcohol at a concentration of about 2% (v/v), and arginine at a concentration of about 0.5 M, having a pH of about 6.0;
(ix) a solution comprising sodium benzoate at a concentration of about 0.5 M, benzyl alcohol at a concentration of about 2% (v/v), and arginine at a concentration of about 0.5 M, having a pH of about 5.0; and
(x) a solution comprising benzyl alcohol at a concentration of about 2% (v/v) and arginine at a concentration of about 0.5 M, having a pH of about 5.0.

9. The method of claim 1, further comprising a step of washing the matrix with a first solution prior to washing the matrix with the wash solution of step (b) in claim 1, wherein the first solution comprises a buffer selected from the group consisting of a phosphate buffer, a tris buffer, an acetate buffer, a carbonate buffer, a citrate buffer, and any combinations thereof, and wherein the concentration of the buffer in the first solution is about 10 mM to about 100 mM.

10. The method of claim 1, further comprising a step of washing the matrix with a second solution after washing the matrix with the wash solution of step (b) in claim 1, wherein the second solution comprises a buffer selected from the group consisting of a phosphate buffer, a tris buffer, an acetate buffer, a carbonate buffer, a citrate buffer, and any combinations thereof, wherein the concentration of the buffer in the second solution is about 10 mM to about 100 mM, wherein the second solution has a pH of about 5.0 to about 7.0, and wherein the second solution comprises no salt.

11. The method of claim 1, further comprising one or more of the following steps:
(i) contacting the Protein A chromatography matrix with an elution solution after one or more washings steps;
(ii) collecting an eluate comprising the polypeptide comprising the Fc region; and
(iii) filtering the eluate via depth filtration.

12. The method of claim 11, wherein the method comprises(ii) collecting an eluate comprising the polypeptide comprising the Fc region, and wherein the eluate comprises less than about 500 parts per million (ppm) of the one or more impurities.

13. The method of claim 1, wherein the method results in the polypeptide comprising the Fc region being purified away from the one or more impurities to a higher degree than a corresponding method lacking the step of washing the matrix with the wash solution, and wherein the one or more impurities are host cell proteins (HCPs) selected from the group consisting of phospholipases, clusterin, serine proteases, elongation factors, and any combinations thereof.

14. The method of claim 13, wherein the HCP is a phospholipase, and wherein the phospholipase is Putative Phospholipase B-like 2 (PLBL2).

15. The method of claim 13, wherein the host cell is a mammalian host cell.

16. The method of claim 1, wherein the Fc region is a human IgG1 Fc region, a human IgG2 Fc region, a human IgG4 Fc region, a mouse IgG1 Fc region, a mouse IgG2 Fc region, or a mouse IgG3 Fc region.

17. The method of claim 1, wherein the polypeptide comprising the Fc region is an antibody.

18. The method of claim 17, wherein the antibody is a human antibody, a humanized antibody, a chimeric antibody, a monoclonal antibody, a bispecific antibody, or a trispecific antibody.

19. The method of claim 1, further comprising, before step (a), adjusting a harvest comprising the polypeptide comprising the Fc region to achieve a final concentration of a benzoate salt of between about 0.1 M and about 0.5 M and a pH between about 7.0 and about 9.0 to produce the sample comprising (i) the polypeptide comprising the Fc region, and (ii) one or more impurities.

20. A method of purifying a polypeptide comprising an Fc region, the method comprising the steps of:
(A) adjusting a harvest comprising the polypeptide comprising the Fc region to achieve a final concentration of a benzoate salt of about 0.1M and about 0.5M and a pH between about 7.0 and about 9.0 to produce a sample comprising (i) the polypeptide comprising the Fc region, and (ii) one or more impurities; and
(B) contacting the sample with at least one chromatography matrix.

* * * * *

UNITED STATES PATENT AND TRADEMARK OFFICE
CERTIFICATE OF CORRECTION

PATENT NO. : 11,236,126 B2
APPLICATION NO. : 16/228291
DATED : February 1, 2022
INVENTOR(S) : Carl A. Beigie It is certified that error appears in the above-identified patent and that said Letters Patent is hereby corrected as shown below:

In the Claims

In Claim 20, Column 44, Line 43: please replace "a benzoate salt of about 0.1M" with -- a benzoate salt of between about 0.1M --.

Signed and Sealed this
Twenty-ninth Day of November, 2022

Katherine Kelly Vidal
*Director of the United States Patent and Trademark Office*